United States Patent

Stack et al.

Patent Number: 5,962,465
Date of Patent: Oct. 5, 1999

[54] AMINOMETHYL-2,3,8,9-TETRAHYDRO-7H-1, 4-DIOXINO-[2,3-E]-INDOL-8-ONES AND DERIVATIVES

[75] Inventors: Gary P. Stack, Ambler; Richard E. Mewshaw, Princeton; Byron A. Bravo, Plainsboro; Young H. Kang, Robbinsville, all of N.J.

[73] Assignee: American Home Products Corporation, Madison, N.J.

[21] Appl. No.: 09/015,149

[22] Filed: Jan. 29, 1998

Related U.S. Application Data

[62] Division of application No. 08/730,267, Oct. 15, 1996, Pat. No. 5,756,532.
[60] Provisional application No. 60/007,283, Nov. 6, 1995.
[51] Int. Cl.[6] .................... C07D 491/113; C07D 491/04; A61K 31/47
[52] U.S. Cl. .................. 514/291; 546/90; 546/18; 544/335; 544/336; 544/322; 514/253; 514/256
[58] Field of Search .................. 546/90, 18; 514/291, 514/253, 256; 544/322, 335, 336

[56] References Cited

U.S. PATENT DOCUMENTS

| | | | |
|---|---|---|---|
| 5,126,366 | 6/1992 | Stack et al. | 514/452 |
| 5,166,367 | 11/1992 | Stack et al. | 549/289 |
| 5,189,171 | 2/1993 | Stack et al. | 546/157 |
| 5,235,055 | 8/1993 | Stack et al. | 546/177 |
| 5,245,051 | 9/1993 | Stack et al. | 549/361 |
| 5,318,988 | 6/1994 | Schche-Loop et al. | 514/458 |

FOREIGN PATENT DOCUMENTS 9113872  9/1991  WIPO .

OTHER PUBLICATIONS

Michael D. Ennis et al., J. Med. Chem, 35, 3058–3066 (1992).

*Primary Examiner*—John M. Ford
*Attorney, Agent, or Firm*—Rebecca R. Barrett

[57] ABSTRACT

The compounds of formula I:

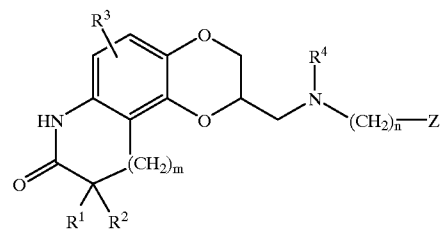

wherein $R^1$ and $R^2$ are, independently, hydrogen, alkyl, phenyl or benzyl; or $R^1$ and $R^2$, taken together, are benzylidene optionally substituted with $R^3$ as defined below or alkylidene, or $R^1$ and $R^2$, taken together with the carbon to which they are attached, form a carbonyl moiety or a cycloalkyl group; $R^3$ is hydrogen, hydroxy, halo, trifluoromethyl, trifluoromethoxy, alkyl, alkoxy, aralkoxy, alkanoyloxy, amino, mono- or di-alkylamino, alkanamido or alkanesulfonamido; $R^4$ is hydrogen or alkyl; m is an integer 0, 1 or 2; n is an integer from 0 to 6, inclusive; Z is hydrogen, hydroxy, alkyl, alkenyl, alkynyl, alkoxy, cycloalkyl, polycyclo-alkyl, phenyl optionally substituted with $R^3$ as defined above, phenoxy optionally substituted with $R^3$ as defined above, naphthyl optionally substituted with $R^3$ as defined above or naphthyloxy optionally substituted with $R^3$ as defined above, heteroaryl or heteroaryloxy, in which the heterocyclic ring of the heteroaryl or heteroaryloxy group is selected from thiophene, furan, pyridine, pyrazine, pyrimidine, indole, indazole, imidazole, chroman, coumarin, carbostyril, quinoline, benzisoxazole, benzoxazole, pyrazole, pyrrole, thiazole, oxazole, or isoxazole and the heterocyclic ring is optionally substituted by $R^3$ as defined above; or a pharmaceutically acceptable salt thereof, are useful in treating disorders of the dopaminergic system.

4 Claims, No Drawings

AMINOMETHYL-2,3,8,9-TETRAHYDRO-7H-1,4-DIOXINO-[2,3-E]-INDOL-8-ONES AND DERIVATIVES

This application is a divisional of U.S. Ser. No. 08/730,267 field Oct. 15, 1996, now U.S. Pat. No. 5,756,532, and claims the benefit of U.S. provisional application No. 60/007,283, filed Nov. 6, 1995 as a continuation-in-part thereof.

BACKGROUND OF THE INVENTION

PCT Int. Appl. WO 91 13,872 discloses dioxino[2,3-e] indole derivatives of the following formula, in which $R^1$ is H, alkyl, $CO_2R^2$, $CONHR^2$, cyano, halo, CHO, etc.; $R^2$ is H, alkyl, $(CH_2)_m$ Y; Y is cycloalkyl or cycloalkenyl, (substituted)phenyl, pyridyl, naphthyl, indolyl; m is 0–6; A and B are O, $CH_2$,S; and X is $CH_2(CH_2)_mNR^2R^2$ as serotonergic and dopaminergic agents useful for the treatment of CNS and cardiovascular disorders.

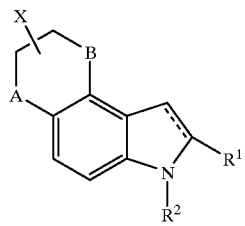

U.S. Pat. No. 5,318,988 discloses 2-aminomethyl-chromans of the following formula as useful for treatment of diseases of the central nervous system. In this group of compounds, A, B and D are identical or different and represent hydrogen, halogen, cyano, azido, nitro, di- or tri-fluoromethyl, di- or tri-fluoromethoxy, hydroxyl or carboxyl, straight-chain or branched-chain alkyl, alkenyl, acyl, alkoxy or alkoxycarbonyl, or a mono- or di-substituted or unsubstituted amino, amido or sulfonamido, or A may be so defined and B and D taken together to form a 5 to 7-membered saturated, partly unsaturated, or aromatic carbocyclic ring or heterocyclic ring

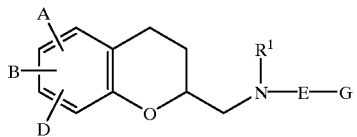

having up to two S, N or O atoms, optionally one or two carbonyl functions in the ring and optionally ring substituted by alkyl, branched alkyl or cycloalkyl; E represents a direct bond or represents straight chain or branched chain alkylene, alkenylene or alkynylene; G represents aryl having 6 to 10 carbon atoms or a 5 to 7-membered, saturated or unsaturated heterocyclic ring which is not bonded via N and has up to 3 hetero atoms from the series comprising N, O or S, to which a further saturated, partly unsaturated or aromatic 6-membered ring can optionally also be fused or cycloalkyl or a bridged bicarbocyclic ring.

U.S. Pat. Nos. 5,126,366, 5,166,367, 5,189,171, 5,235,055 and 5,245,051 describe a series of antipsychotic agents of the formula

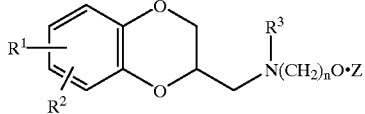

in which Z represents aminophenoxy, coumarin, carbostyril, quinoline or chroman; $R^1$ and $R^2$ are, independently, hydrogen, alkyl, alkoxy, aralkoxy, alkanoyloxy, hydroxy, halo, amino, mono- or di-alkylamino, alkanamido, or alkanesulfonamido or $R^1$ and $R^2$ together are methylenedioxy, ethylenedioxy or propylenedioxy; $R^3$ is hydrogen or alkyl; n is one of the integers 2, 3 or 4.

DESCRIPTION OF THE INVENTION

In accordance with this invention, there is provided a group of novel anti-psychotic agents of formula I:

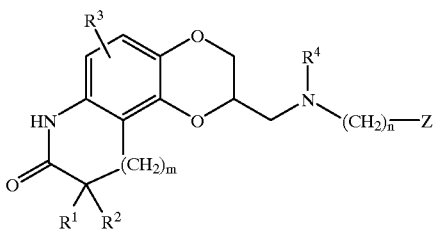

wherein $R^1$ and $R^2$ are, independently, hydrogen, alkyl of 1 to 6 carbon atoms, phenyl or benzyl; or $R^1$ and $R^2$, taken together, are benzylidene optionally substituted with $R^3$ as defined below or alkylidene of 1 to 6 carbon atoms, or $R^1$ and $R^2$, taken together with the carbon to which they are attached, form a carbonyl moiety or a cycloalkyl group having 3 to 6 carbon atoms;

$R^3$ is hydrogen, hydroxy, halo, trifluoromethyl, trifluoromethoxy, alkyl of 1 to 6 carbon atoms, alkoxy of 1 to 6 carbon atoms, arylalkoxy of 7 to 12 carbon atoms, alkanoyloxy of 2 to 6 carbon atoms, amino, mono- or di-alkylamino in which each alkyl group has 1 to 6 carbon atoms, alkanamido of 2 to 6 carbon atoms or alkanesulfonamido of 1 to 6 carbon atoms;

$R^4$ is hydrogen or alkyl of 1 to 6 carbon atoms;

m is one of the integers 0, 1 or 2;

n is one of the integers 0, 1, 2, 3, 4, 5, or 6;

Z is hydrogen, hydroxy, alkyl of 1 to 6 carbon atoms, alkenyl of 2 to 6 carbon atoms, alkynyl of 2 to 6 carbon atoms, alkoxy of 1 to 6 carbon atoms, cycloalkyl of 3 to 8 carbon atoms, polycyclic alkyl of 7 to 15 carbon atoms, phenyl optionally substituted with $R^3$ as defined above, phenoxy optionally substituted with $R^3$ as defined above, naphthyl optionally substituted with $R^3$ as defined above or naphthyloxy optionally substituted with $R^3$ as defined above, heteroaryl or heteroaryloxy, in which the heterocyclic ring of the heteroaryl or heteroaryloxy group is selected from thiophene, furan, pyridine, pyrazine, pyrimidine, indole, indazole, imidazole, chroman, coumarin, carbostyril, quinoline, benzisoxazole, benzoxazole, pyrazole, pyrrole, thiazole, oxazole, or isoxazole and the heterocyclic ring is optionally substituted by $R^3$ as defined above;

or a pharmaceutically acceptable salt thereof.

Of these compounds, the preferred members are those in which $R^1$ and $R^2$ are hydrogen or together form benzylidene optionally substituted with $R^3$ as defined above or, taken together with the carbon to which they are attached, form a carbonyl moiety, $R^3$ and n are defined as above, $R^4$ is hydrogen, m is 0 or 1, and Z is hydrogen, hydroxy, alkyl of 1 to 6 carbon atoms, cycloalkyl of 3 to 8 carbon atoms, polycyclic alkyl of 7 to 15 carbon atoms, phenyl optionally substituted with $R^3$ as defined above, phenoxy optionally substituted with $R^3$ as defined above, naphthyl optionally substituted with $R^3$ as defined above or naphthyloxy, optionally substituted with $R^3$ as defined above, heteroaryl or heteroaryloxy, the heterocyclic ring of the heteroaryl or heteroaryloxy groups being selected from thiophene, furan, pyridine, pyrimidine, indole, indazole, chroman, coumarin, carbostyril, quinoline, benzisoxazole, benzoxazole, and the hetero ring is optionally substituted by $R^3$ as defined above.

Most preferred are those members in which $R^1$, $R^2$ and $R^4$ are hydrogen, m is 0, and $R^3$, Z and n are defined as in the previous paragraph. This invention relates to both the R and S stereoisomers of the benzodioxan methanamine, as well as to mixtures of the R and S stereoisomers. Throughout this application, the name of the product of this invention, where the absolute configuration of the benzodioxan methanamine is not indicated, is intended to embrace the individual R and S enantiomers as well as mixtures of the two.

The pharmaceutically acceptable salts are those derived from such organic and inorganic acids as: acetic, lactic, citric, tartaric, succinic, fumaric, maleic, malonic, mandelic, mallic, hydrochloric, hydrobromic, phosphoric, nitric, sulfuric, methanesulfonic, toluenesulfonic and similarly known acceptable acids.

Aminomethyl-2,3,8,9-tetrahydro-7H-1,4-dioxino[2,3-e]indol-8-ones are prepared as outlined below. Specifically, the appropriately substituted nitroguaiacol is alkylated with allyl bromide in the presence of a suitable base such as sodium hydride and then

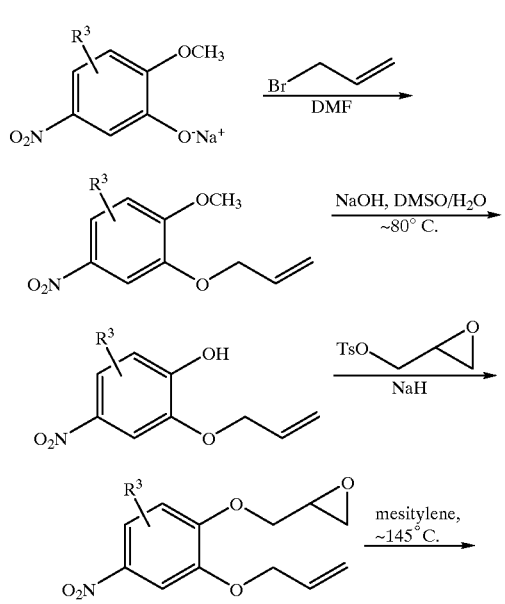

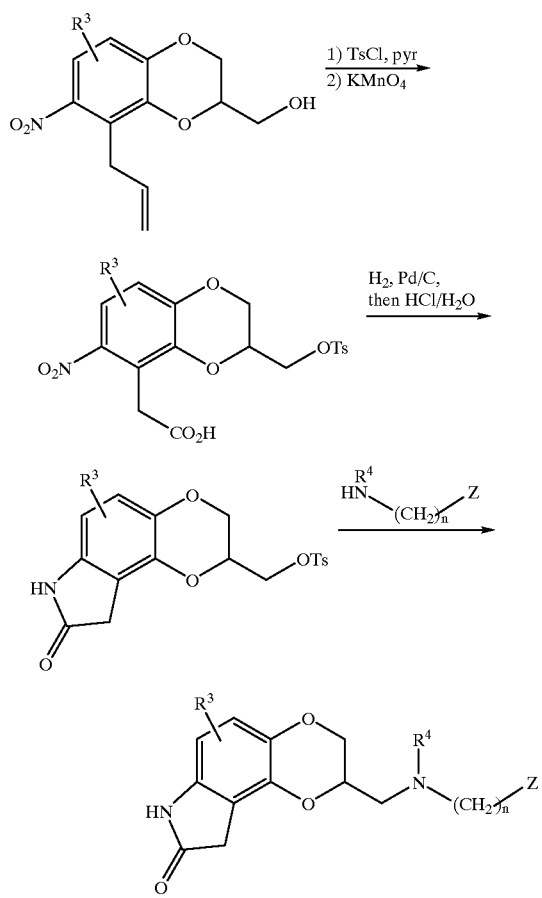

demethylated by a reagent such as sodium hydroxide. The resulting 4-nitro-2-allyloxyphenol is then alkylated with glycidyl tosylate or an epihalohydrin in the presence of a base such as sodium hydride and heated in a high boiling solvent such as mesitylene or xylene to effect both rearrangement of the allyl group and cyclization of the dioxan ring. The resulting primary alcohol is converted to the tosylate by reaction with p-toluenesulfonyl chloride in the presence of pyridine or alternatively to a halide by reaction with carbon tetrabromide or carbon tetrachloride in combination with triphenylphosphine. The allyl side chain is converted to an acetic acid moiety by oxidative cleavage with potassium permanganate and the nitro group is reduced to an amine with hydrogen and palladium on carbon and cyclized to the lactam with aqueous hydrochloric acid. Replacement of the tosylate or halide with a suitably substituted amine in some high boiling solvent such as dimethyl sulfoxide gives the title compounds of the invention.

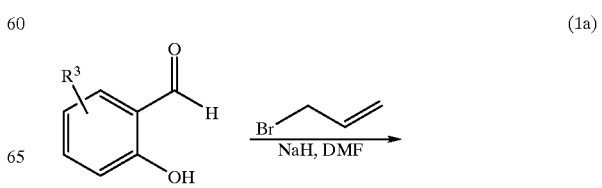

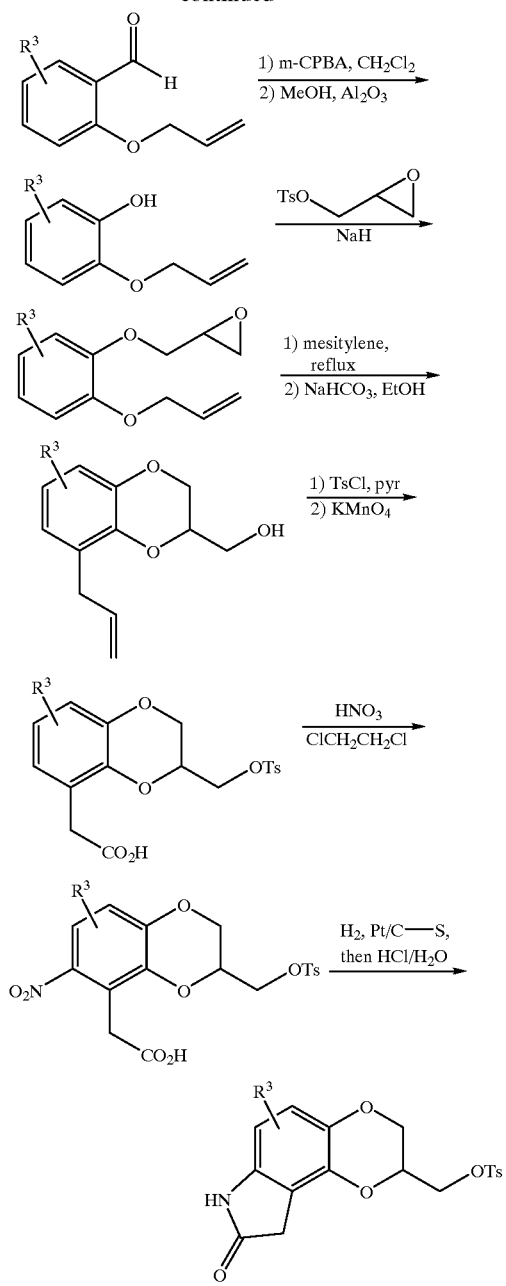

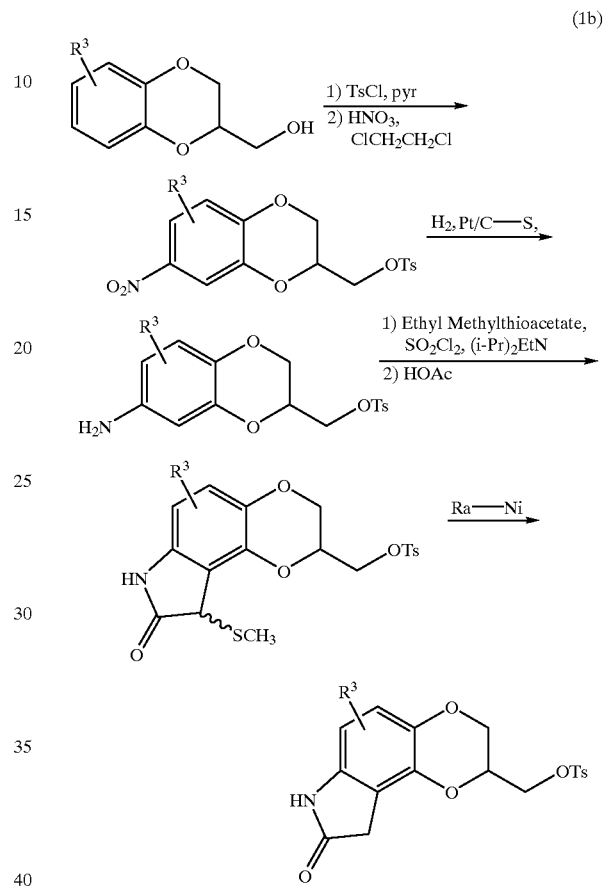

The oxindoledioxan methyltosylate described in (1) may also be prepared as in (1a) above: the appropriately substituted salicylaldehyde is alkylated with allyl bromide in the presence of a suitable base such as sodium hydride. The aldehyde moiety is then converted to a phenol by treatment with m-chloroperoxybenzoic acid followed by cleavage of the intermediate formate ester with basic alumina in methanol. The resulting 2-allyloxyphenol is then alkylated with glycidyl tosylate or an epihalohydrin in the presence of a base such as sodium hydride and heated in a high boiling solvent such as mesitylene or xylene to effect the rearrangement of the allyl group. Cyclization to the benzodioxan-methanol is completed by treatment with sodium bicarbonate in ethanol. Following conversion of the alcohol to a tosylate via p-toluenesulfonyl chloride in pyridine, the allyl side chain is oxidatively cleaved to an acetic acid moiety with potassium permanganate and the nitro group introduced by treatment with nitric acid in dichloroethane. Reduction of the nitro group and cyclization to the lactam are effected as in (1). A catalyst such as platinum oxide or platinum on sulfided carbon is preferred for the reduction when $R^3$ is a halogen.

The oxindoledioxan methyltosylate may also be prepared from the appropriately substituted benzodioxan methanol as in (1b) above. Following conversion of the alcohol to the tosylate as described above, the nitro function is introduced by treatment with nitric acid in dichloroethane and reduced with hydrogen in the presence of a suitable catalyst such as platinum oxide or platinum on sulfided carbon. The oxindole is elaborated by a modification of the procedure of Gassman et. al. [*J. Amer. Chem. Soc.* 96, 5512 (1974)] and the resulting thiomethyl ether cleaved by treatment with Raney nickel.

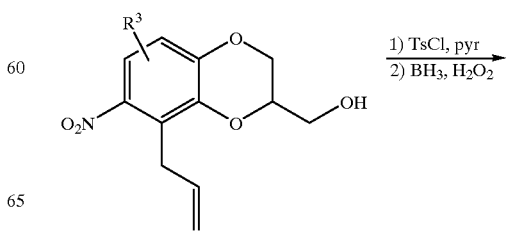

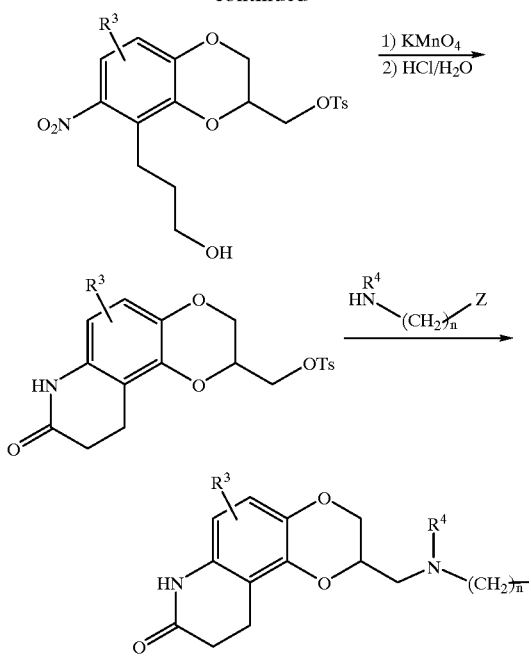

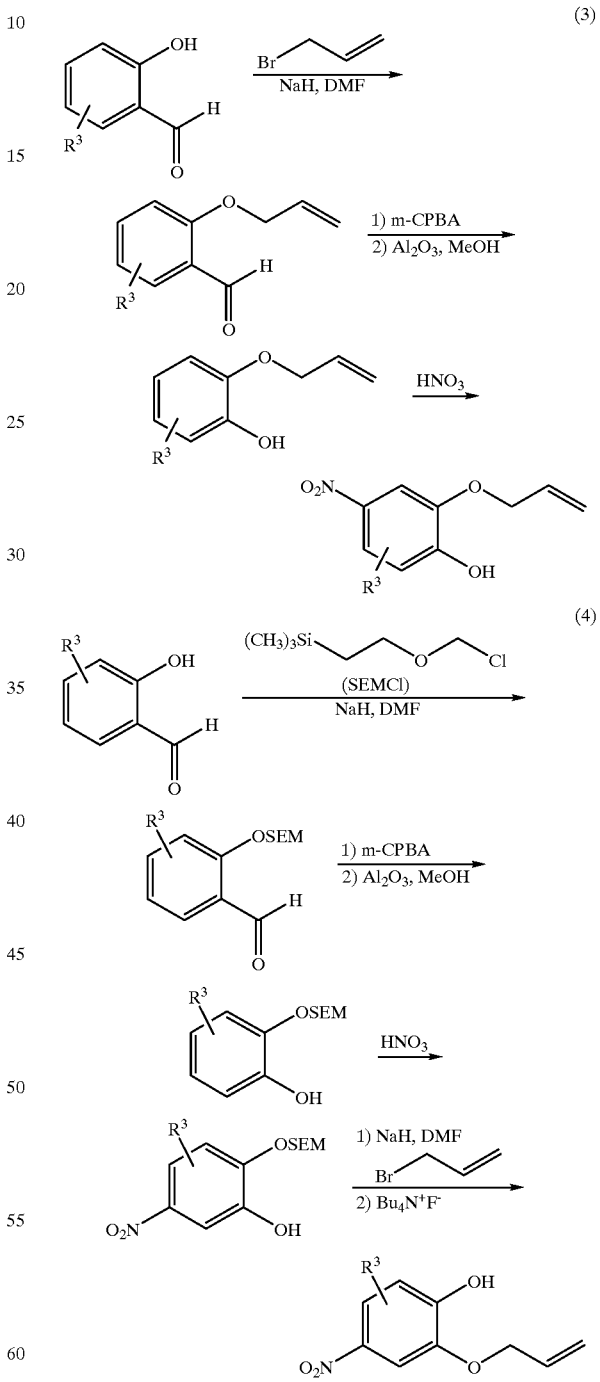

Alternatively, the allyl side chain may be converted to a propyl alcohol residue by hydroboration with borane/THF followed by treatment with hydrogen peroxide as shown above. The primary alcohol may be oxidized to a carboxylic acid with a suitable oxidizing agent such as potassium permanganate and cyclized to the lactam as before with aqueous hydrochloric acid. Replacement of the tosylate or halide with the suitably substituted amine in some high boiling solvent such as dimethyl sulfoxide as above gives the compounds of the invention in which m is 1. A similar strategy in which the propyl alcohol is converted to a bromide by treatment with carbon tetrabromide and triphenylphosphine, replaced with cyanide by treatment with sodium cyanide in dimethylformamide and hydrolyzed to the homologous acid may be employed to prepare compounds of the invention in which m is 2, provided the benzodioxan methanol is suitably protected throughout this procedure.

Compounds of the invention in which $R^1$ and $R^2$ combine to form a benzylidene or alkylidene residue may be prepared by condensation of the lactams described above with the appropriate aromatic or aliphatic aldehyde. Compounds of the invention in which $R^1$ and $R^2$ are alkyl may be prepared by alkylation of the intermediate carboxylic acids or their corresponding esters under standard conditions. Compounds of the invention in which $R^1$ and $R^2$ combine to form a carbonyl (i.e., isatins) may be prepared by oxidation of the corresponding oxindoles. The appropriate nitroguaiacols are known compounds or may be prepared by one schooled in the art. Alternatively, the 4-nitro-2-allyloxyphenols utilized in process (1) described above may be prepared from the appropriately 5- or 6-substituted salicylaldehyde by procedure (3) below, or from the appropriately 3- or 4-substituted salicylaldehyde by procedure (4) below, in which [2-(trimethylsilyl)ethoxy]methyl chloride (SEMCl) is employed as a hydroxy protecting group during conversion of the aldehyde to the formate ester with meta-chloroperbenzoic acid followed by hydrolysis to the hydroxy group. The substituted amines, $R^4$—$NH(CH_2)_n$—Z, are known compounds or may be readily prepared by one schooled in the art. The compounds of the invention may be resolved into their enantiomers by conventional methods or, preferably, they may be prepared directly by substitution of (2R)-(−)-glycidyl 3-nitrobenzenesulfonate or tosylate (for the S benzodioxan methanamine) or (2S)-(+)-glycidyl 3-nitrobenzenesulfonate or tosylate (for the R enantiomer) in place of epihalohydrin or racemic glycidyl tosylate in the procedures above.

The compounds of this invention are dopamine autoreceptor agonists; that is, they serve to modulate the synthesis and release of the neurotransmitter dopamine. These compounds also act as partial agonists at the postsynaptic dopamine $D_2$ receptor, capable of functioning as either agonists or antagonists depending on the level of dopaminergic stimulation. They thus serve to modulate dopaminergic neurotransmission and are thereby useful for treatment of disorders of the dopaminergic system, such as schizophrenia, schizoaffective disorder, Parkinson's disease, Tourette's syndrome and hyperprolactinemia and in the treatment of drug addiction such as the addiction to ethanol or cocaine and related illnesses.

The effect of the compounds of the invention on the synthesis of dopamine was established by the method of Walters and Roth, Naunyn-Schmiedeberg's Arch. Pharmacol. 296:5–14, 1976, in which rats (male, Sprague-Dawley, Charles River, 200–350 g) were administered vehicle or test drug ten minutes prior to the administration of gamma butyrolactone (GBL; 750 mg/kg, ip to inhibit dopaminergic impulse flow) and 20 minutes prior to NSD-1015 (100 mg/kg, ip to prevent the conversion of dopa to dopamine). Thirty minutes after NSD-1015 all rats were decapitated and the nucleus accumbens and the striatum were removed for analysis. Following perchloric acid extraction of the tissue, the extracts were placed over alumina columns to collect and concentrate dopa and other catechols. This eluate was then subjected to HPLC analysis using electrochemical detection to quantify the levels of dopa present. Dopamine autoreceptor agonists, under the conditions used above, inhibit dopa accumulation. When tested in this model, the compound of Example 1, representative of the other compounds of the invention, inhibits dopa accumulation by 67.5% at a dose of 10 mg/kg, sc.

The antipsychotic activity of the compounds of the invention was further established by a determination of the compounds' ability to reduce mouse locomotor activity according to the method of Martin and Bendensky, J. Pharmacol. Exp. Therap. 229: 706–711, 1984, in which mice (male, CF-1, Charles River, 20–30 g) were injected with vehicle or various doses of each drug and locomotor activity was measured for 30 minutes using automated infrared activity monitors (Omnitech—8×8 inch open field) located in a darkened room. $ED_{50}$'s were calculated from the horizontal activity counts collected from 10 to 20 minutes after dosing using a nonlinear regression analysis with inverse prediction. The results of this test with compounds of the invention are reported below.

Affinity for the dopamine $D_2$ receptor was established by a modification of the standard experimental test procedure of Seemen and Schaus, European Journal of Pharmacology 203: 105–109, 1991, wherein homogenized rat striatal brain tissue is incubated with $^3$H-quinpirole and various concentrations of test compound, filtered and washed and counted in a Betaplate scintillation counter. The results of this testing with compounds representative of this invention are also given below.

The results of the standard experimental test procedures described in the preceding two paragraphs were as follows:

| Compound | Hypolocomotion ($ED_{50}$ mg/kg, sc) | $D_2$ Receptor Affinity ($IC_{50}$ (nM)) |
| --- | --- | --- |
| Example 1 | 0.0031 | 0.37 |
| Example 2 |  | 2.80 |
| Example 3 | 0.039 | 0.14 |
| Example 4 |  | 1.79 |
| Example 5 |  | 1.42 |
| Example 6 |  | 12.25 |
| Example 7 | 0.005 | 0.34 |
| Example 8 |  | 9.93 |
| Example 9 |  | 0.37 |
| Example 10 |  | 3.06 |
| Example 11 | 0.0138 | 1.30 |
| Example 12 | 0.0005 | 0.51 |
| Example 13 |  | 1.39 |
| Example 14 | 0.008 | 0.43 |
| Example 15 | 0.09 | 3.33 |
| Example 16 |  | 0.45 |
| Example 17 | 0.027 | 0.68 |
| Example 18 |  | 0.49 |
| Example 19 |  | 0.34 |
| Example 20 |  | 0.29 |
| Example 21 |  | 0.33 |
| Example 22 |  | 17.70 |
| Example 23 |  | 0.89 |
| Example 24 |  | 8.80 |
| Example 25 |  | 1.04 |
| Example 26 |  | 0.52 |
| Example 28 | 0.024 | 1.39 |
| Example 29 |  | 3.30 |
| Example 31 |  | 1.30 |
| Example 32 |  | 2.15 |
| Example 33 |  | 0.57 |
| Example 34 |  | 0.56 |
| Example 35 |  | 52.10 |
| Example 36 |  | 0.35 |
| Example 37 |  | 0.51 |
| Example 38 |  | 1.08 |
| Example 39 | 0.064 | 0.78 |
| Example 40 |  | 0.53 |
| Example 41 |  | 0.56 |
| Example 42 |  | 0.67 |
| Example 43 |  | 0.98 |
| Example 44 |  | 1.43 |
| Example 45 |  | 0.97 |
| Example 46 |  | 1.00 |

Hence, the compounds of this invention have potent affinity for dopamine receptors and markedly effect the synthesis of the neurotransmitter dopamine. They are, therefore, useful in the treatment of dopaminergic disorders such as schizophrenia, schizoaffective disorder, Parkinson's disease, Tourette's syndrome, hyperprolactinemia and drug addiction.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient. Based upon the activity profile and potency of the compounds of this invention compared to the clinically useful antipsychotic risperidone, it is considered that a starting dose of about 5 mg per day with gradual in crease in the daily dose-to about 75 mg per day will provide the desired dosage level in the human.

The following examples illustrate the production of representative compounds of this invention.

INTERMEDIATE 1

3-Allyloxy-4-methoxynitrobenzene 97.5 g (0.51 mole) of the sodium salt of 5-nitroguaiacol was dissolved in one liter of DMF and 1.5 equivalents of allyl bromide added. The reaction was heated to 65° C. for two hours, after which time much of the dark color had discharged and tlc (1:1 $CH_2Cl_2$/hexane) indicated loss of starting material. The solvent was concentrated in vacuum and the residue washed with water. The product was isolated by filtration and dried in a vacuum. This gave 112 g of pale yellow solid. A sample recrystallized from methanol, gave m.p. 93–94° C.

INTERMEDIATE 2

2-Allyloxy-4-nitrophenol

To one liter of dimethyl sulfoxide was added 750 ml of 2 N aqueous sodium hydroxide and the mixture was heated to 65° C. The pale yellow solid 3-allyloxy-4-methoxynitrobenzene prepared above was added in portions over a 30 minute period and then the temperature was raised to 95° C. and maintained for 3 hours, after which time the starting material had been consumed. The mixture was allowed to cool and poured into a mixture of 1L ice and 1L 2 N HCl. 73 Grams of crude but homogeneous (by tlc 1:1 $CH_2Cl_2$/hexane) desired product was isolated as a light brown solid by filtration. This material was subsequently dissolved in 1:1 hexane/methylene chloride and filtered through silica gel to give 68 g of pale yellow solid, which, when recrystallized from ethyl/acetate/hexane, gave m.p. 61–62° C. The aqueous mother liquors from the initial crystallization above were extracted with 2L of ethyl acetate. This was dried over sodium sulfate, filtered and evaporated to a dark oil. Column chromatography on silica with 1:1 $CH_2Cl_2$/hexane gave an additional 12 g of the title compound as a yellow solid. Elution with 2% MeOH in $CHCl_3$ gave 12 g of a dark oil which slowly crystallized in vacuum. This proved to be the Claisen product, 3-allyl-4-nitrocatechol.

INTERMEDIATE 3

2-(2-Allyloxy-4-nitrophenoxymethyl)-oxirane 20 g (0.50 mole) of 60% NaH/mineral oil was placed in a two liter flask and washed with 500 ml of hexane. 1L of DMF was added, followed by 77 g (0.40 mole) of the 2-allyloxy-4-nitrophenol prepared in the previous step. Addition of the phenol was performed in portions under argon. After stirring the mixture for 30 minutes at room temperature under argon, 108 g (0.48 moles) of (R)-glycidyl tosylate was added and the mixture heated at 70–75° C. under nitrogen overnight. Upon cooling, the DMF was removed in vacuum and replaced with one liter of methylene chloride. This was washed with 500 ml portions of 2 N HCl, saturated sodium bicarbonate and saturated brine and dried over sodium sulfate. The mixture was filtered, concentrated to an oil in vacuum and column chromatographed on silica gel using 1:1 hexane/methylene chloride as eluant. This gave 43 g of product contaminated with traces of the two starting materials, followed by 21 g of pure product as a pale yellow solid. The impure material was recrystallized from 1.2L of 10% ethyl acetate/hexane to give 34 g of pure (homogeneous on silica gel tlc with 1:1 hexane/methylene chloride) (R)-2-(2-allyloxy-4-nitrophenoxymethyl)-oxirane (m.p. 64° C).

Elemental Analysis for: C12H13NO5, Calc'd: C, 57.37; H, 5.21; N, 5.58, Found: C, 57.50; H, 5.21; N, 5.43

INTERMEDIATE 4

(8-Allyl-7-nitro-2,3-dihydro-benzo(1,4)dioxin-2-yl)-methanol (R)-2-(2-Allyloxy-4-nitrophenoxymethyl)-oxirane (20 g, 80 mmoles) prepared as above was heated at 155° C. in mesitylene for 24 hours under nitrogen. Filtration of the black solid which formed gave 1.5 g of very polar material. Evaporation of the solvent in vacuum followed by column chromatography on silica gel with methylene chloride as eluant gave 10 g of recovered starting material and 7.5 g of the desired rearranged (S)-(8-allyl-7-nitro-2,3-dihydro-benzo(1,4)dioxin-2-yl)-methanol, which slowly crystallized on standing in vacuum (m.p. 67° C.). The yield based on recovered starting material is 75%.

Elemental Analysis for: $C_{12}H_{13}NO_5$; Calc'd: C, 57.37; H, 5.21; N, 5.58; Found: C, 57.26; H, 5.20; N, 5.35

INTERMEDIATE 5

Toluene-4-sulfonic acid allyl-7-nitro-2,3-dihydro-benzo(1,4)dioxin-2-ylmethyl ester 9.55 g (38.0 mmole) of (S)-(8-allyl-7-nitro-2,3-dihydro-benzo(1,4)dioxin-2-yl)-methanol was dissolved in 465 ml of pyridine, 29.0 g (152 mmole) of p-toluenesulfonyl chloride was added and the mixture stirred at room temperature under nitrogen overnight. Water was then added to quench the excess tosyl chloride and the solvent was removed in vacuum and replaced with methylene chloride. This solution was washed with 2 N HCl, with saturated sodium bicarbonate, and with saturated brine, and dried over magnesium sulfate. Filtration, evaporation in vacuum and column chromatography on silica gel with 1:1 hexane/methylene chloride as eluant gave 12.6 g (92%) of toluene-4-sulfonic acid (R)-allyl-7-nitro-2,3-benzo(1,4)dioxin-2-ylmethyl ester, which slowly crystallized to a tan solid (m.p. 60–62° C.) upon standing.

Elemental Analysis for: $C_{19}H_{19}NO_7S$; Calc'd: C, 56.29; H, 4.72; N, 3.45; Found: C, 56.13; H, 4.58; N, 3.44

INTERMEDIATE 6

(6-Nitro-3-(toluene-4-sulfonyloxymethyl)-2,3-dihydro-benzo(1,4)dioxin-5-yl)-acetic acid Potassium permanganate (11.7 g, 0.074 mole) was placed in a flask which was equipped with a mechanical stirrer, a dropping funnel, and an ice bath. To this was added 150 ml of $H_2O$ and tetrabutylammonium chloride (1.0 g, 3.7 mmole) with stirring. The toluene-4-sulfonic acid (R)-allyl-7-nitro-2,3-benzo(1,4)dioxin-2-ylmethyl ester prepared above dissolved in 100 ml of benzene was slowly added through a dropping funnel and the reaction mixture was stirred further for 30 minutes in an ice bath. The ice bath was then removed and the mixture was stirred for 24 hours at room temperature. 30 g of sodium bisulfite was added to the mixture with good stirring in an ice bath and acidified with concentrated HCl until pH<3. The acidified clear yellow solution was then extracted with ethyl acetate and the combined extracts were dried over anhydrous magnesium sulfate. The concentrated residue was chromatographed on a silica gel column using ethyl acetate as an eluant to give 6.3 g (60%) of (R)-(6-nitro-3-(toluene-4-sulfonyloxymethyl)-2,3-dihydro-benzo(1,4)-dioxin-5-yl)-acetic acid as a pale yellow solid. Crystallization from methylene chloride gave a light yellow solid with m.p. 158–159° C.

Elemental Analysis for: $C_{18}H_{17}NO_9S.¼ H_2O$; Calc'd: C, 50.52; H, 4.12; N, 3.27; Found: C, 50.51; H, 3.83; N, 3.12

INTERMEDIATE 7

2-(Toluene-4-sulfonyloxymethyl)-2,3,8,9-tetrahydro-7H-1,4-dioxino[2,3-e]-indol-8-one The carboxylic acid (6.0 g, 0.0142 mole) obtained above was ground into a fine powder. To this was added 300 ml of water and 5 ml of 2.5 N NaOH until the pH was 8, and the heterogeneous solution was stirred for 30 minutes until the solid was evenly dispersed. 1.0 g of 10% Pd on carbon was then added and the mixture was hydrogenated on a Parr shaker for 24 hours at 52 psi of hydrogen. The catalyst was filtered off and washed with water. The volume of the filtrate was then reduced by half and acidified with 15 ml of concentrated HCl while stirring in an ice bath to precipitate a white solid acid product, (R)-(6-amino-3-(toluene-4-sulfonyloxymethyl)-2,3-dihydro-benzo(1,4)dioxin-5-yl)-acetic acid. This heterogeneous solution was then heated at 50° C. for 24 hours. As time passed, tlc (5% methanol/$CH_2Cl_2$ on silica gel) showed that the amino acid was slowly replaced with lactam, and the reaction mixture became clear briefly and then the title compound started to precipitate as a white solid After the mixture was cooled to room temperature and stirred for an additional hour, the white solid was filtered, washed with diethyl ether and dried in a vacuum at room temperature. The product (R)-2-(toluene-4-sulfonyloxymethyl)-2,3,8,9-tetrahydro-7H-1,4-dioxino[2,3-e]indol-8-one_(m.p. 225–227° C.) was pure without further recrystallization and weighed 4.2 g (79%).

Elemental Analysis for: $C_{18}H_{17}NO_6S$; Calc'd: C, 57.59; H, 4.57; N, 3.73; Found: C, 57.34; H, 4.55; N, 3.69

EXAMPLE 1

2-(Benzylamino-methyl)-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (0.80 g, 2.13 mmole) and 99.5% benzylamine (1.42 g, 11.72 mmole) were combined in 15 ml of dry DMSO, with a heavy stream of $N_2$ bubbled through the solution. This was heated to 75° C. for 3 hours. The reaction was cooled and taken into 400 ml of ethyl acetate. This was washed with six 100 ml portions of water. The combined aqueous washes were back-extracted with six 50 ml portions of ethyl acetate. The organic fractions were combined, washed with brine, dried over $MgSO_4$, filtered and concentrated to yield a brown oil. This oil was column chromatographed on silica gel using 0.75% methanol/$CH_2Cl_2$ to remove impurities. A concentration of 1% methanol/$CH_2Cl_2$ eluted the desired product, which was obtained as an oil (1.85g, 65%). This oil was crystallized from isopropanol with the addition of a solution of fumaric acid (0.76 g, 6.57 mmole) in hot isopropanol to give 2.21 g of the (S) enantiomer of the title compound as a light yellow solid monofumarate, quarter hydrate, m.p. 202° C.

Elemental Analysis for: $C_{18}H_{18}N_2O_3 \cdot C_4H_4O_4 \cdot 0.25 H_2O$; Calc'd: C, 61.32; H, 5.26; N, 6.50; Found: C, 61.3 1; H, 5.01; N, 6.42

EXAMPLE 2

2-(Benzylamino-methyl)-1-benzylidene-2,3,8,9-tetrahydro-7H-1,4-dioxino[2,3-e]indol-8-one The title compound was isolated as a side product upon prolonged heating of the reaction described in Example 1. The benzylamine employed in this reaction was subsequently determined to contain approximately 0.5% benzaldehyde. The title compound was readily isolated via silica gel column chromatography using 0.75% methanol/$CH_2Cl_2$ as eluant. The condensation product was obtained as an orange oil and crystallized with the addition of a solution of fumaric acid in hot isopropanol to give 0.30 g of a bright orange solid half fumarate, quarter hydrate, of (S) configuration, m.p. 206° C.

Elemental Analysis for: $C_{25}H_{22}N_2O_3 \cdot 0.50 C_4H_4O_4 \cdot 0.25 H_2O$; Calc'd: C, 70.35; H, 5.36; N, 6.08; Found: C, 70.31;H, 5.13; N, 6.04

EXAMPLE 3

2-{[3-(Indol-3-yl)-propylamino]-methiyl}-2,3,8,9-tetrahydro-7H-1,4-dioxino-[2,3-e]indol-8-one (R)-2-(Toluene-4-sulfonyloxymethyl)-2,3,8,9-tetrahydro-7H-1,4-dioxino[2,3-e]indol-8-one (1.5 g, 4.2 mmole) in DMSO (80 ml) was slowly added through a dropping funnel to 3-(3-aminopropyl)indole (1.1 g, 6.3 mmole) in DMSO (50 ml) and the mixture was heated at 75° C. for 17 hours. Most of DMSO was removed under reduced pressure and the residue was then partitioned between water and dichloromethane/isopropanol (3/1) solution. The separated organic layer was dried over anhydrous sodium sulfate, filtered, concentrated in vacuum and column chromatographed on silica gel using first ethyl acetate/hexane (7/3), then ethyl acetate and finally 5% methanol in ethyl acetate as eluants. The expected product was isolated, treated with 0.25 M ethanolic fumaric acid and precipitated with a minimum amount of hexane to give 70 mg of the (S) enantiomer of the title compound as a tan solid fumarate salt, Mass spec (m/e), 377 (M+).

EXAMPLE 4

2-{[2-(1H-Indol-3-yl)-ethylamino]-methyl}-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (1.2 g, 3.2 mmole) and tryptamine (1.5 g, 9.6 mmole) in DMSO (50 ml) were placed in a three-neck flask equipped with a condenser, a thermometer and a nitrogen bubbler immersed into the solution. The reaction mixture was heated at 75° C. for 5 hours, cooled to room temperature and partitioned between water and ethyl acetate. The ethyl acetate layer was separated, dried over anhydrous sodium sulfate, concentrated in vacuum and column chromatographed on silica gel using first ethyl acetate and subsequently 2.5%, 5%, 10% methanol in ethyl acetate as eluants. The free base of the desired product was obtained (0.85 g, 2.3 mmole) as an oil which was dissolved in 50 ml of ethanoldiethyl ether (1/1) solution and treated with 10.3 ml of 0.25 M of fumaric acid in ethanol. Addition of hexane gave 0.30 g of the (S) enantiomer of the title compound as an off-white solid hemi-fumarate, three quarter hydrate, m.p. 175–176° C.

Elemental Analysis for: $C_{21}H_{21}N_3O_3 \cdot \frac{1}{2} C_4H_4O_4 \cdot \frac{3}{4} H_2O$, Cacl'd: C, 63.51; H, 5.68; N, 9.66, Found: C, 63.51; H, 5.75; N, 9.47

EXAMPLE 5

2-[(3-Hydroxy-propylamino)-methyl]-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (0.37 g, 1.0 mmole) in 3-amino-1-propanol (20 ml) was heated at 75° C. for 15 hours. The heterogeneous reaction began to clear up during this period. The reaction mixture was cooled to room temperature and partitioned between dichloromethane/IPA (3/1) solution and brine. The separated aqueous layer was extracted with dichioromethane/IPA (3/1), and the combined extracts were washed with saturated sodium bicarbonate solution and water to remove aminopropanol, dried over anhydrous sodium sulfate and concentrated in vacuum. The residue was chromatographed on an alumina (basic) column using 5% methanol in dichloromethane as eluent to give the free base (0.2 g, 72%) of the expected product. The free base was dissolved in ethanol (10 ml), treated with excess of 0.25 M ethanolic fumaric acid and precipitated with hexane to give 0.090 g of the (S) enantiomer of the title compound as a pale yellow solid hemi-fumarate, quarter hydrate, m.p. 192–193° C.

Elemental Analysis for: $C_{14}H_{18}N_2O_4 \cdot \frac{1}{2} C_4H_4O_4 \cdot \frac{1}{4} H_2O$; Cacl'd: C, 56.38; H, 6.06; N, 8.22; Found: C, 56.31; H, 6.13; N, 8.00

EXAMPLE 6

2-(Benzyl amino-methyl)-2,3,9,10-tetrahydro-7H-1,4-dioxino[2,3-f]quinolin-8-one

A 1M solution of $BH_3 \cdot THF$ (11.00 ml, 11.00 mmole) was placed in a 100 ml round-bottom flask equipped with $N_2$ line, dropping funnel and thermometer. The solution was cooled to 0° C. in an ice-water bath. To this cooled solution was added dropwise, (R)-toluene-4-sulfonic acid 8-allyl-7-nitro-2,3-dihydro-benzo[1,4]dioxin-2-ylmethyl ester (2.25 g, 5.56 mmole) in 10 ml of dry THF over a 10 minute period. The reaction was allowed to reach room temperature and then stirred overnight. It was then cooled to 0° C. and to it was added dropwise 2.42 ml of absolute ethanol and 6.16 ml (18.5 mmole) of a 3 N NaOH solution. After a few minutes, 4.2 ml of a 30% aqueous $H_2O_2$ solution was added over a 20 minute period. The mixture was heated to 48° C. for three hours. The mixture was then cooled to 0° C. and to it was added 6.08 g of $K_2CO_3$. The mixture was stirred for 0.5 hr and then left standing overnight. The following morning the solid had disappeared. The reaction was diluted with water and extracted with ethyl acetate. The organic layer washed with brine, dried over $MgSO_4$, filtered and concentrated to yield a clear viscous oil (1.20 g, 51%) of (R)-toluene-4-sulfonic acid 8-(3-hydroxy-propyl)-7-nitro-2,3-dihydro-benzo[1,4]dioxin-2-ylmethyl ester.

To a 50 ml 3-neck flask equipped with magnetic stirrer, thermometer, $N_2$ line and dropping funnel, was added $KMnO_4$ (1.24 g, 9.25 mmole), $H_2O$ (15 ml) and tetra-n-butylammonium chloride (0.17 g). The purple solution was cooled to 0° C. and to it was added dropwise the (R)-toluene-4-sulfonic acid 8-(3-hydroxy-propyl)-7-nitro-2,3-dihydro-benzo[1,4]dioxin-2-ylmethyl ester (1.20 g, 2.84 mmole) prepared above in 10.3 ml of benzene. The reaction was stirred at room temperature overnight and then 4.40 g of sodium bisulfite was added. The color of the mixture was discharged after five minutes' stirring. After an addtional 10 minutes' stirring, 4 N isopropanolic HCl was added to bring the pH to about 1. The mixture was diluted with water and extracted with ethyl acetate. The organic layer was washed four times with 50 ml of brine, dried over $MgSO_4$, filtered and concentrated to yield a clear yellow oil (0.95 g, 77%) of 3-[6-nitro-3-(toluene-4-sulfonyloxymethyl)-2,3-dihydro-benzo[1,4]dioxin-5-yl]-propionic acid.

3-[6-Nitro-3-(toluene-4-sulfonyloxymethyl)-2,3-dihydro-benzo[1,4]dioxin-5-yl]-propionic acid (0.95 g, 2.17 mmole) was taken into 8 ml of isopropanol and transferred to a Parr bottle. To this solution was added water (50 ml), a 2.5 N solution of NaOH (0.83 g) and methanol (30 ml). The solution was flushed with a heavy stream of $N_2$ and to it added 10% Pd/C (0.32 g). The mixture was hydrogenated on a Parr apparatus at 57 psi of $H_2$. After twenty hours, the mixture was filtered and the catalyst washed with water. To the aqueous filtrate was added 2.3 ml of concentrated HCl and the solution was heated overnight at 55° C. When the solution had cooled, 0.45 g of (R)-2-(tosylate-methyl)-2,3,9,10-tetrahydro-7H-1,4-dioxino[2,3-f]quinolin-8-one precipitated and was collected by filtration and dried in vacuum.

(R)-2-(Toluene-4-sulfonyloxymethyl)-2,3,9,10-tetrahydro-7H-1,4-dioxino-[2,3-f]quinolin-8-one (0.45 g, 1.16 mmole) and 99.5% benzylamine (0.68 g, 6.33 mmole) were combined in 15 ml of dry DMSO and heated to 80° C. for 7 hours under a nitrogen atmosphere. To this reaction was added 150 ml of water and this was extracted with ethyl acetate. The organic layer was washed with brine, dried over $MgSO_4$, filtered and concentrated to yield a light brown solid. This solid was column chromatographed on silica gel using 0.75% methanol/$CH_2Cl_2$ to remove impurities. A concentration of 4% methanol/$CH_2Cl_2$ eluted the desired product, which was obtained as a white solid (0.29 g, 77%). This solid was crystallized from isopropanol with the addition of a solution of fumaric acid (0.11 g, 0.94 mmole) in hot isopropanol to give 0.32 g of the (S) enantiomer of the title compound as a light white solid monofumarate, m.p. 219° C.

Elemental Analysis for: $C_{19}H_{20}N_2O_3 \cdot C_4H_4O_4$; Calc'd: C, 62.72; H, 5.49; N, 6.36; Found: C, 62.34; H, 5.32; N, 6.19

EXAMPLE 7

(2-[(4-Methyl-benzylamino)-methyl]-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (0.80 g, 2.13 mmole) and 4-methylbenzylamine (1.42 g, 11.7 mmole) were combined in 15 ml of dry DMSO and heated to 85° C. for 4 hours under a nitrogen atmosphere. The reaction was cooled and partitioned between 70 ml of ethyl acetate and 200 ml of deionized $H_2O$. The organic layer was washed with brine, dried over $MgSO_4$, filtered and concentrated to yield a brown-orange oil. This oil was column chromatographed on silica gel using 0.75% methanol/$CH_2Cl_2$ to remove impurities. A concentration of 2% methanol/$CH_2Cl_2$ eluted the desired product, which was isolated as an oil (0.40 g, 58%). The oil was crystallized from isopropanol with the addition of a solution of fumaric acid (0.16 g, 1.36 mmole) in hot isopropanol to give 0.39 g of the (S) enantiomer of the title compound as an off-white solid fumarate salt, m.p. 204–205° C., which was contaminated by an additional half equivalent of fumaric acid.

Elemental Analysis for: $C_{25}H_{26}N_2O_9 \cdot 1.5\ C_4H_4O_4$; Calc'd: C, 60.24; H, 5.26; N, 5.62; Found: C, 60.18; H, 5.26; N, 5.79

EXAMPLE 8

2-Aminomethyl-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (3.0 g, 8.0 mmole) and sodium azide (1.6 g, 24.0 mmole) were placed in 300 ml of DMF and the reaction mixture was heated at 45° C. for 15 hours. Most of the DMF was removed and the residue was partitioned between dichloromethane and water. The dichloromethane layer was separated, dried over anhydrous magnesium sulfate and concentrated. The residue was pure enough without further purification and was identified as the desired product, (S)-2-azidomethyl-2,3,8,9-tetrahydro-7H-1,4-dioxino[2,3-e]indol-8-one. An aliquot amount of the azide (0.8 g, 3.2 mmole) in ethanol (50 ml) was hydrogenated with 10% palladium on carbon (100 mg) for 15 hours. The resulting mixture was acidified with 4 N isopropanolic HCl until pH<3. The catalyst was then filtered off and the filtrate was concentrated. The residue was dissolved in 90% aqueous ethanol and precipitated with diethyl ether to give the (S) enantiomer of the title compound as a white solid hydrochloride, 1.25 hydrate, (0.7 g, 85%), m.p. 278–280° C.

Elemental Analysis for: $C_{11}H_{12}N_2O_3 \cdot HCl \cdot 1.25\ H_2O$; Cacl'd: C, 47.32; H, 5.59; N, 10.03; Found: C, 47.48; H, 5.44; N, 10.08

EXAMPLE 9

2-(Cyclohexylmethylamino-methyl)-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (0.80 g, 2.13 mmole), and cyclohexylmethylamine (1.33 g, 11.7 mmole) were combined in 15 ml of dry DMSO and heated to 80° C. for 6 hours under a nitrogen atmosphere. The reaction was allowed to cool and was partitioned between 100 ml of ethyl acetate and 150 ml of deionized water. The organic layer was washed with brine, dried over $MgSO_4$, filtered and concentrated to yield a black oil. This oil was column chromatographed on silica gel using 0.75% methanol/$CH_2Cl_2$ to remove impurities. A concentration of 2% methanol/$CH_2Cl_2$ eluted the desired product, which was as an oil (0.38 g, 56%) upon concentration in vacuum. This oil was crystallized from isopropanol with the addition of a solution of fumaric acid (0.15 g, 1.3 mmole) in hot isopropanol to give 0.39 g of the (S) enantiomer of the title compound as an off-white solid monofumarate, half hydrate, m.p. 187–188° C.

Elemental Analysis for: $C_{18}H_{24}N_2O_3 \cdot C_4H_4O_4 \cdot 0.5\ H_2O$; Calc'd: C, 59.85; H, 6.62; N, 6.34; Found: C, 59.81; H, 6.61; N, 6.28

EXAMPLE 10

2-[(2-Pyridin-3yl-ethylamino)-methyl]-2,3,8,9-tetrahydro-7H-1,4-dioxino-[2,3-e]indol-8-one (R)-2-(Toluene-4-sulfonyloxymethyl)-2,3,8,9-tetrahydro-7H-1,4-dioxino[2,3-e]indol-8-one (0.80 g, 2.1 mmole) and 3-(2-aminoethyl)pyridine (1.30 g, 10.6 mmole) were combined in 15 ml of dry DMSO and heated to 85° C. for 9 hours under a nitrogen atmosphere. The reaction was allowed to cool and then was partioned between methylene chloride and deionized water. The aqueous layer was extracted with additional methylene chloride. The organic fractions were combined, washed with brine, dried over $MgSO_4$, filtered and concentrated to yield an orange oil. This oil was column chromatographed on silica gel using 0.75% methanol/$CH_2Cl_2$ to remove impurities. A concentration of 3–5% methanol/$CH_2Cl_2$ eluted the desired product, which was obtained as a beige solid (0.48 g, 69%) upon concentration in vacuum. This was recrystallized from isopropanol with the addition of 4 N isopropanolic HCl to give 0.27 g of the (S) enantiomer of the title compound as a light yellow solid dihydrochloride, 0.75 hydrate, m.p. 174–176° C.

Elemental Analysis for: $C_{18}H_{19}N_3O_3 \cdot 2\ HCL \cdot 0.75\ H_2O$; Calc'd: C, 52.50; H, 5.51; N, 10.00; Found: C, 52.19; H, 6.29; N, 10.00

EXAMPLE 11

2-{[3-(3-Dimethylamino-phenoxy)-propylamino]-methyl}-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (0.80 g, 2.13 mmole) and 3-(3-dimethylaminophenoxy)propylamine (2.07 g, 10.6 mmole) were combined in 15 ml of dry DMSO and heated to 85° C. for 4 hours under a nitrogen atmosphere. The reaction was taken into 150 ml of methylene chloride and washed six times with 40 ml portions of water. The organic layer was washed with brine, dried over $MgSO_4$, filtered and concentrated in vacuum to yield a brown oil. The oil was column chromatographed on silica gel using 0.75% methanol/$CH_2Cl_2$ to remove impurities. A concentration of 12% methanol/$CH_2Cl_2$ eluted the desired product, which was obtained as an oil (0.27 g, 32%) upon concentration in vacuum. The oil was crystallized from isopropanol with the addition of a solution of fumaric acid (0.086 g, 0.75 mmole) in hot isopropanol to give 0.17 g of the (S) enantiomer of the title compound as a brown solid, monofumarate, m.p. 136–138° C.

Elemental Analysis for: $C_{22}H_{27}N_3O_4 \cdot C_4H_4O_4$; Calc'd: C, 60.81; H, 6.08; N, 8.18; Found: C, 61.17; H, 6.21; N, 8.3

EXAMPLE 12

2-{[(Thiophen-2-ylmethyl)-amino]-methyl}-2,3,8,9-tetrabydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (0.80 g, 2.13 mmole) and thiophene-2-methylamine (1.45 g, 12.80 mmole) were combined in 15 ml of dry DMSO and heated to 85° C. for 6 hours under a nitrogen atmosphere. The reaction was taken into 150 ml of methylene chloride and washed six times with 40 ml portions of water. The organic layer was washed with brine, dried over $MgSO_4$, filtered and concentrated in vacuum to yield a dark orange oil. This oil was column chromatographed on silica gel using 0.75% methanoV/$CH_2Cl_2$ to remove impurities. A concentration of 1–2% methanol/$CH_2Cl_2$ eluted the desired product, which was obtained as an oil (0.44 g, 54%) after concentration in vacuum. The crude product was crystallized from isopropanol with the addition of a solution of fumaric acid (0.18 g, 1.5 mmole) in hot isopropanol to give 0.48 g of the (S) enantiomer of the title compound as a light yellow solid monofumarate, quarter hydrate, m.p. 210–211° C.

Elemental Analysis for: $C_{16}H_{16}N_2O_3S.C_4H_4O_4.0.25 H_2O$:; Calc'd: C, 54.98; H, 4.73; N, 6.41; Found: C, 55.03; H, 4.70; N, 6.23

EXAMPLE 13

2-{[3-(Quinolin-7-yloxy)-propylamino]-methyl}-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (0.80 g, 2.13 mmole) and 3-(quinolin-7-yloxy)propylamine (2.15 g, 10.6 mmole) were combined in 15 ml of dry DMSO and heated to 85° C. for 6 hours under a nitrogen atmosphere. The reaction was taken into 150 ml of methylene chloride and washed six times with 40 ml portions of water. The organic layer was washed with brine, dried over $MgSO_4$, filtered and concentrated to yield a dark brown oil. This oil was column chromatographed on silica gel using 0.75% methanol/$CH_2Cl_2$ to remove impurities. A concentration of 4–5% methanol/$CH_2Cl_2$ eluted the desired product, which was obtained as a beige solid (0.30 g, 35%) after concentration in vacuum. The crude solid was recrystallized from isopropanol with the addition of 4 N isopropanolic HCl to give 0.14 g of the (S) enantiomer of the title compound as a light yellow solid dihydrochloride, hydrate, m.p. 176–177° C.

Elemental Analysis for: $C_{23}H_{23}N_3O_4.2 HCl.H_2O$; Calc'd: C, 55.65; H, 5.48; N, 8.46; Found: C, 55.48; H, 5.98; N, 8.36

EXAMPLE 14

(2{[(Adamantan-1-ylmethyl)-aminol]-methyl}-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (0.70 g, 1.87 mmole) and 1-adamantanemethylamine (1.55 g, 9.35 mmole) were combined in 15 ml of dry DMSO and heated to 85° C. for 6 hours under a nitrogen atmosphere. The reaction was taken up in 150 ml of ethyl acetate and washed six times with 40 ml portions of water. The organic layer was washed with brine, dried over $MgSO_4$, filtered and concentrated in vacuum to yield a dark brown oil. The oil was column chromatographed on silica gel using 0.75% methano/$CH_2Cl_2$ as eluant to give 0.51 g (74%) of the desired product as a beige solid. The crude product was recrystallized from isopropanol with the addition of a solution of fumaric acid (0.18 g, 1.5 mmole) in hot isopropanol to give 0.49 g of the (S) enantiomer of the title compound as an off-white solid monofumarate, half hydrate, m.p. 201–202° C.

Elemental Analysis for: $C_{22}H_{28}N_2O_3.C_4H_4O_4.0.5 H_2O$; Calc'd: C, 63.25; H, 6.78; N, 5.67; Found: C, 63.23; H, 6.87; N, 5.60

EXAMPLE 15

2-(Benzylamino-methyl)-2,3,8,9-tetrahydro-7H-1,4-dioxino[2,3-e]indol-8-one (S)-2-(Toluene-4-sulfonyloxymethyl)-2,3,8,9-tetrahydro-7H-1,4-dioxino[2,3-e]indol-8-one (2.0 g, 5.3 mmole), prepared in the same manner as the (R) enantiomer described above with substitution of (S)- for (R)-glycidyl tosylate, and benzylamine (2.9 ml, 26.7 mmole) were placed in 20 ml of fresh DMSO under nitrogen. The mixture was then heated to 75–80° C. with stirring for 3 hours. After cooling to room temperature, the reaction mixture was partitioned between ethyl acetate and brine. The DMSO layer was extracted with ethyl acetate and the combined ethyl acetate extracts were washed with water to remove trace DMSO, dried over anhydrous sodium sulfate and concentrated in vacuum. The residue was chromatographed on a silica gel column using ethyl acetate as the eluant to yield the free base (1.4 g, 4.5 mmole, 83%) of the expected product as a solidified oil under reduced pressure. The free base was dissolved in 20 ml of ethanol, treated with 0.25 M ethanolic fumaric acid (10 ml) and precipitated with diethyl ether to give the title compound as a pale yellow solid fumarate salt, predominantly in the (R)-configuration, m.p. 195–196° C. This sample, from which the pharmacological results reported in this application were obtained, was determined by chiral HPLC to contain 9% of the (S)-enantiomer.

Elemental Analvsis for: $C_{18}H_{18}N_2O_3.C_4H_4O_4$; Cacl'd: C, 61.97; H, 5.20; N, 6.57; Found: C, 61.96; H, 5.13; N, 6.51

EXAMPLE 16

2-(Pentylaminomethyl)-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (0.80 g, 2.13 mmole) and pentylamine (0.93 g, 10.6 mmole) were combined in 15 ml of dry DMSO and heated to 85° C. for 6 hours under a nitrogen atmosphere. The reaction taken up in 150 ml of $CH_2Cl_2$ and washed with six 40 ml portions of water. The organic layer was washed with brine, dried over $MgSO_4$, filtered and concentrated in vacuum to yield a brown oil, which was column chromatographed on silica gel using 0.75% methanol/$CH_2Cl_2$ to remove impurities. A concentration of 1–2% methanol/$CH_2Cl_2$ eluted the desired product, which was obtained as an oil (0.20 g, 32%) upon concentration in vacuum. The product was crystallized from isopropanol with the addition of a solution of fumaric acid (0.090 g, 0.77 mmole) in hot isopropanol to give 0.10 g of the (S) enantiomer of the title compound as an off-white solid hemifumarate, m.p. 238–239° C.

Elemental Analysis for: $C_{16}H_{22}N_2O_3.0.5 C_4H_4O_4$; Calc'd: C, 62.05; H, 6.94; N, 8.04; Found: C, 61.54; H, 6.89; N, 7.92

EXAMPLE 17

2-[(4-Methoxy-benzylamino)-methyl]-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (1.00 g, 2.66 mmole) and 4-methoxybenzylamine (1.40 ml, 10.7 mmole) were combined in 10 ml of dry DMSO and heated to 85° C. for 3.5 hours under a nitrogen atmosphere. After cooling to room temperature, 150 ml of water was added and the mixture was extracted twice with 250 ml portions of 35% ethyl acetate in hexane. The combined organic phases were washed with brine, dried over $MgSO_4$, filtered and concentrated in vacuum to yield an oil, which was column chromatographed on silica gel using 2% methanol/$CH_2Cl_2$ as eluant. The free base of the title compound (0.51 g, 64%) was obtained as an oil upon concentration in vacuum. The product was crystallized from ethanol with the addition of one equivalent of fumaric acid to give 0.44 g of the (S) enantiomer of the title compound as an off-white solid fumarate, one-quarter hydrate, m.p. 205–205.5° C.

Elemental Analysis for: $C_{19}H_{20}N_2O_4 \cdot C_4H_4O_4 \cdot 0.25\ H_2O$; Calc'd: C, 59.93; H, 5.36; N, 6.08; Found: C, 59.93; H, 5.23; N, 6.14

EXAMPLE 18

2-(Napthalen-1-yl-methylamino-methyl)-2,3,8,9-tetrahydro-7H-1,4-dioxono[2,3-e]indol-8-one (R)-2-(Toluene-4-sulfonyloxymethyl)-2,3,8,9-tetrahydro-7H-1,4-dioxino[2,3-e]indol-8-one (1.05 g, 2.80 mmole) and 1-naphthalenemethylamine (2.05 ml, 14 mmole) were combined in 15 ml of dry DMSO and heated to 85° C. for 4 hours under a nitrogen atmosphere. After cooling to room temperature, 150 ml of water was added and the mixture was extracted twice with 250 ml portions of 35% ethyl acetate in hexane. The combined organic extracts were washed with brine, dried over $MgSO_4$, filtered and concentrated in vacuum to yield an oil, which was column chromatographed on silica gel using 1% methanol/$CH_2Cl_{12}$ as eluant. The free base of the title compound (0.27 g, 27%) was obtained as an oil upon concentration in vacuum. The product was crystallized from ethanol with the addition of one equivalent of fumaric acid to give 0.25 g of the (S) enantiomer of the title compound as an light yellow solid fumarate, one-half hydrate, m.p. 167–168° C.

Elemental Analysis for: $C_{22}H_{20}N_2O_3 \cdot C_4H_4O_4 \cdot 0.5\ H_2O$; Calc'd: C, 64.32; H, 5.19; N, 5.77; Found: C, 64.19; H, 5.48; N, 5.47

EXAMPLE 19

2-(4-Trifluoromethyl-benzylamino-methyl)-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (1.03 g, 2.75 mmole) and 4-trifluoromethylbenzylamine (1.60 ml, 11.2 mmole) were combined in 15 ml of dry DMSO and heated to 85° C. for 3.5 hours under a nitrogen atmosphere. After cooling to room temperature, 150 ml of water was added and the mixture was extracted twice with 250 ml portions of 35% ethyl acetate in hexane. The combined organic phases were washed with brine, dried over $MgSO_4$, filtered and concentrated in vacuum to yield an oil, which was column chromatographed on silica gel using 5% methanol/$CH_2Cl_2$ as eluant. The free base of the title compound (0.56 g, 54%) thus obtained was crystallized from ethanol with the addition of one equivalent of fumaric acid to give 0.06 g of the (S) enantiomer of the title compound as an off-white solid fumarate, m.p. 211–212° C.

Elemental Analysis for: $C_{19}H_{17}F_3N_2O_3 \cdot C_4H_4O_4$; Calc'd: C, 55.87; H, 4.28; N, 5.67; Found: C, 55.56; H, 3.93; N, 5.75

EXAMPLE 20

2-(4-Fluoro-benzylamino)-methyl-2,3,8,9-tetrahydro-7H-1,4-dioxino[2,3-e]-indol-8-one (R)-2-(Toluene-4-sulfonyloxymethyl)-2,3,8,9-tetrahydro-7H-1,4-dioxino[2,3-e]indol-8-one (1.15 g, 3.07 mmole) and 4-fluorobenzylamine (1.56 ml, 13.6 mmole) were combined in 15 ml of dry DMSO and heated to 85° C. for 3.5 hours under a nitrogen atmosphere. After cooling to room temperature, 150 ml of water was added and the mixture was extracted twice with 250 ml portions of 50% ethyl acetate in hexane. The combined organic phases were washed with brine, dried over $MgSO_4$, filtered and concentrated in vacuum to yield an oil, which was column chromatographed on silica gel using 0.75% methanol/$CH_2Cl_2$ as eluant. The free base of the title compound (0.62 g, 62%) thus obtained was crystallized from ethanol with the addition of one equivalent of fumaric acid to give 0.69 g of the (S) enantiomer of the title compound as an off-white solid fumarate, m.p. 218–220° C.

Elemental Analysis for: $C_{18}H_{17}FN_2O_3 \cdot C_4H_4O_4$; Calc'd: C, 59.46; H, 4.76; N, 6.30; Found: C, 59.04; H, 4.67; N, 6.23

EXAMPLE 21

2-(4-Phenyl-butylamino)-methyl-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (1.05 g, 2.80 mmole) and phenylbutylamine (1.99 ml, 12.5 mmole) were combined in 15 ml of dry DMSO and heated to 85° C. for 4 hours under a nitrogen atmosphere. After cooling to room temperature, 200 ml of water was added and the mixture was extracted twice with 300 ml portions of 50% ethyl acetate in hexane. The combined organic phases were washed with brine, dried over $MgSO_4$, filtered and concentrated in vacuum to yield an oil, which was column chromatographed on silica gel using 1% methanol/$CH_2Cl_2$ as eluant. The free base of the title compound (0.26 g, 30%) thus obtained was crystallized from ethanol with the addition of one equivalent of fumaric acid to give 0.25 g of the (S) enantiomer of the title compound as an tan solid fumarate, one-half hydrate, m.p. 185–186° C.

Elemental Analysis for: $C_{21}H_{24}N_2O_3 \cdot C_4H_4O_4 \cdot 0.5\ H_2O$; Calc'd: C, 62.88; H, 6.12; N, 5.87; Found: C, 62.88; H, 6.04; N, 5.79

EXAMPLE 22

2-(4-Fluoro-benzylamino-methyl)-9-(4-fluoro-phenyl-ethylidene)-2,3,8,9-tetrahydro-7H-1,4-dioxino[2,3-e]indol-8-one The title compound was isolated as a side product upon prolonged heating of the reaction described in Example 20. The 4-fluorobenzylamine employed in this reaction was subsequently determined to contain 4-fluorobenzaldehyde. The title compound was isolated from the earlier fractions of the chromatography described in Example 20. The condensation product was obtained as an orange oil and crystallized with the addition of a solution of fumaric acid in hot ethanol to give 0.06 g of an orange solid half fumarate, half hydrate of (S) configuration, m.p. 202° C.

Elemental Analysis for: $C_{25}H_{20}F_2N_2O_3 \cdot 0.5\ C_4H_4O_4 \cdot 0.5\ H_2O$; Calc'd: C, 63.27; H, 4.39; N, 5.09; Found: C, 65.01; H, 4.53; N, 5.58

EXAMPLE 23

N-(3-{3-[(8-Oxo-2,3,8,9-tetrahydro-7H-1,4-dioxino[2.3-e]indol-2-ylmethyl)-amino]-propoxy}-phenyl)-acetaniide (R)-2-(Toluene-4-sulfonyloxymethyl)-2,3,8,9-tetrahydro-7H-1,4-dioxino[2,3-e]indol-8-one (1.04 g, 2.77 mmole) and 3-(3-acetamidophenoxy)propylamine (2.6 g, 12.5 mmole) were combined in 15 ml of dry DMSO and heated to 85° C. for 3.5 hours under a nitrogen atmosphere. After cooling to room temperature, 200 ml of water was added and the mixture was extracted twice with 250 ml portions of 50% ethyl acetate in hexane. The combined organic phases were washed with brine, dried over $MgSO_4$, filtered and concentrated in vacuum to yield an oil, which was column chromatographed on silica gel using 2% methanol/$CH_2Cl_2$ as eluant. The free base of the title compound (0.68 g, 62%) thus obtained was crystallized from ethanol with the addition of one equivalent of fumaric acid to give 0.56 g of the (S) enantiomer of the title compound as a light yellow solid one-half fumarate, one-half hydrate, m.p. 197–198° C.

Elemental Analysis for: $C_{22}H_{25}N_3O_5 \cdot 0.5\ C_4H_4O_4 \cdot 0.5\ H_2O$; Calc'd: C, 61.23; H, 5.93; N, 8.79; Found: C, 60.64; H, 6.06; N, 8.56

EXAMPLE 24

2-(Prop-2-ynylaminomethyl)-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (1.03 g, 2.75 mmole) and propargylamine (0.85 ml, 12.3 mmole) were combined in 20 ml of dry DMSO and heated to 85° C. for 3.5 hours under a nitrogen atmosphere. After cooling to room temperature, 100 ml of water was added and the mixture was extracted twice with 200 ml portions of 50% ethyl acetate in hexane. The combined organic phases were washed with brine, dried over $MgSO_4$, filtered and concentrated in vacuum to yield an oil, which was column chromatographed on silica gel using 1% methanol/$CH_2Cl_2$ as eluant. The free base (0.50 g, 71%) thus obtained was crystallized from isopropanol with the addition of one equivalent of fumaric acid to give 0.42 g of the (S) enantiomer of the title compound as a light yellow solid fumarate, m.p. 167–168° C.

Elemental Analysis for: $C_{14}H_{14}N_2O_3 \cdot C_4H_4O_4$; Calc'd: C, 57.75; H, 4.85; N, 7.48; Found: C, 57.93; H, 5.16; N, 7.28

EXAMPLE 25

2-[(3-Trifluoromethyl-benzylamino)-methyl]-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (1.01 g, 2.70 mmole) and 3-trifluoromethylbenzylamine (1.75 ml, 12.0 mmole) were combined in 15 ml of dry DMSO and heated to 85° C. for 4 hours under a nitrogen atmosphere. After cooling to room temperature, 200 ml of water was added and the mixture was extracted twice with 250 ml portions of 50% ethyl acetate in hexane. The combined organic phases were washed with brine, dried over $MgSO_4$, filtered and concentrated in vacuum to yield an oil, which was column chromatographed on silica gel using 2% methanol/$CH_2Cl_2$ as eluant. The free base of the title compound (0.20 g, 20%) thus obtained was crystallized from isopropanol with the addition of one equivalent of fumaric acid to give 0.17 g of the (S) enantiomer of the title compound as a light yellow solid fumarate, one-half hydrate, m.p. 158–160° C.

Elemental Analsis for: $C_{19}H_{17}F_3N_2O_3 \cdot C_4H_4O_4 \cdot 0.5\ H_2O$; Calc'd: C, 54.87; H, 4.41; N, 5.56; Found: C, 54.70; H, 4.09; N, 5.57

EXAMPLE 26

2-(Benzylamino-methyl)-2,3-dihydro-7H-1,4-dioxino[2,3-e]indole-8,9-dione 0.60 g (1.94 mmole) of (S)-2-(benzylamino-methyl)-2,3,8,9-tetrahydro-7H-1,4-dioxino[2,3-e]indol-8-one prepared as in Example 1 was taken into 200 ml of 1N NaOH and 150 ml methanol and stirred without protection from air for 48 hrs, neutralized and extracted with ethyl acetate. Concentration of the organic phase yielded 200 mg of a dark red oil. This oil was crystallized from isopropanol with the addition of a solution of fumaric acid (79 mg, 0.68 mmole) in hot isopropanol to yield 0.12 g of the (S) enantiomer of the title compound as a dark red solid, m.p. 177° C. (d).

Elemental Analysis for: $C_{19}H_{17}F_3N_2O_3 \cdot C_4H_4O_4$; Calc'd: C, 55.87; H, 4.28; N, 5.67; Found: C, 55.56; H, 3.93; N, 5.75

EXAMPLE 27

2-[(4-Trifluoromethoxy-benzylamino)-methyl]-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (1.0 g, 2.7 mmole) and 4-trifluoromethoxybenzylamine (2.0 g, 11 mmole) were combined in 30 ml of dry DMSO and heated to 90° C. for 4 hours under an argon atmosphere. After cooling to room temperature, the mixture was diluted with 400 ml of 1:1 ethyl acetate/hexane and washed with 400 ml of saturated sodium bicarbonate solution, with two 250 ml portions of water and with saturated brine. The mixture was dried over sodium sulfate, filtered and concentrated in vacuum to yield an oil, which was column chromatographed on silica gel using 1% methanol/$CHCl_3$ as eluant. The free base of the title compound (0.49 g) thus obtained was crystallized from ethanol with the addition of one equivalent of fumaric acid to give 0.29 g of the (S) enantiomer of the title compound as a white solid fumarate, m.p. 201–202° C.

Elemental Analysis for: $C_{19}H_{17}F_3N_2O_3 \cdot C_4H_4O_4$; Calc'd: C, 54.12; H, 4.15; N, 5.49; Found: C, 55.80; H, 3.97; N, 5.36

INTERMEDIATE 8

(R)-2-Toluene-4-sulfonyloxymethyl)-6-methyl-2,3-dihydrobenzo[1,4]dioxin (S)-(6-methyl-2,3-dihydrobenzo(1,4 dioxin-2-yl)-methanol (10.1 g, 56.2 mmole) was dissolved in 375 ml of pyridine. To this solution was added 21.4 g (0.11 mole) of p-toluenesulfonyl chloride and the mixture stirred at room temperature under nitrogen overnight. The reaction was cooled in an ice-water bath and to it was added slowly 400 ml of water. The mixture was stirred at room temperature for 4 hours and then the solvent was removed under vacuum to yield a dark brown oil. This was dissolved in ethyl acetate and washed with 2 N HCl (aq), with water, and with saturated brine and dried over $MgSO_4$. Filtration, evaporation in vacuum and column chromatography on silica gel with 40% hexane in dichloromethane as eluent gave 15.1 g (89%) of the title compound as a colorless oil. $^1H$ ($CDCl_3$) doublet, 7.80 δ (2 H); doublet, 7.38 δ (2 H); singlet, 6.61 δ (3 H); envelope, 4.40–3.90 δ (5 H); singlet, 2.40 δ (3 H); singlet, 2.20 δ (3 H).

INTERMEDIATE 9

(R)-2-Toluene-4-sulfonyloxymethyl)-6-methyl-7-nitro-2,3-dihydrobenzo[1,4]dioxin (R)-2-Toluene-4-sulfonyloxymethyl)-6-methyl-2,3-dihydrobenzo[1,4]dioxin (15.1 g, 50 mmole) was dissolved in 154 ml of dichloroethane and cooled to 0° C. in an ice/water bath. To this cooled solution was added dropwise over a 10 minute period a solution of nitric acid (sp. gr. 1.49) in 38 ml of dichloroethane. The mixture was stirred at 0° C.

under nitrogen for one hour, after which time the reaction was quenched by the addition of ice. The mixture was diluted with methylene chloride and washed with saturated aqueous sodium bicarbonate solution, with water, with saturated brine and dried over magnesium sulfate. Filtration and evaporation in vacuum gave 16.8 g of the title compound as a yellow solid. $^1$H (DMSO-$d_6$) doublet, 7.80 δ (2 H); doublet, 7.45 δ (2 H); singlet, 7.40 δ (1 H);.singlet, 6.98 δ (1 H); multiplet, 4.57 δ (1 H); multiplet, 4.40 δ (2 H); multiplet, 4.20 δ (1 H); multiplet, 4.10 δ (1 H); singlet, 2.43 δ (3 H); singlet, 2.40 δ (3 H).

INTERMEDIATE 10

(R)-2-Toluene-4-sulfonyloxymethyl)-6-methyl-7-amino-2,3-dihydrobenzo[1,4]-dioxin (R)-2-Toluene-4-sulfonyloxymethyl)-6-methyl-7-nitro-2,3-dihydrobenzo[1,4]-dioxin (16.8 g, 44.6 mmole) was added to a suspension of 1.8 g of 10% palladium on carbon in 150 ml of methanol. The mixture was hydrogenated overnight using a Parr apparatus at 58 psi of hydrogen. The mixture was then filtered through celite and the catalyst washed with ethyl acetate. The filtrate was concentrated in vacuum to give 11.7 g of the title compound as a light yellow solid. $^1$H (DMSO-$d_6$) doublet, 7.80 δ (2 H); doublet, 7.48 δ (2 H); singlet, 6.40 δ (1 H); singlet, 6.08 δ (1 H); singlet, 4.40 δ (2 H); multiplet, 4.30 δ (2 H); multiplet, 4.10 δ (2 H); multiplet, 3.80 δ (1 H); singlet, 2.40 δ (3 H); singlet, 1.90 δ (3 H).

INTERMEDIATE 11

(R)-2-(Toluene-4-sulfonyloxymethyl)-6-methyl-2,3,8,9-tetrahydro-7H-1,4-dioxino[2,3-e]indol-8-one In a three-neck flask equipped with a dropping funnel, thermometer and a nitrogen inlet was placed 5.56 g (41.4 mmole) of ethyl methylthioacetate and 130 ml of dry methylene chloride. The solution was cooled to –78° C. by means of a dry ice/isopropanol bath and to it was added dropwise 5.20 g (38.4 mmole) of sulfuryl chloride over a 3 minute period. To the resulting mixture was added dropwise over a 15 minute period a solution of (R)-2-toluene-4-sulfonyloxymethyl)-6-methyl-7-amino-2,3-dihydrobenzo[1,4]dioxin (11.7 g, 33.6 mmole) and Proton Sponge (8.64 g, 40.3 mmole) in 220 ml of methylene chloride. The mixture was stirred a –78° C. for two hours, then 5.2 g (40.3 mmole) of diisopropylethylamine was added dropwise over a 10 minute period and stirring continued for an additional hour at –78° C., after which the reaction was allowed to come to room temperature at which temperature it was stirred overnight under nitrogen. The resulting solution was diluted to 500 ml with methylene chloride and washed with saturated brine, dried over magnesium sulfate, filtered and concentrated in vacuum to a brown oil. This was dissolved in 140 ml of glacial acetic acid and stirred for 1.5 hour at room temperature under a nitrogen atmosphere. The solvent was then removed in vacuum and replaced with 500 ml of methylene chloride. The mixture was washed with 300 ml portions of saturated aqueous sodium bicarbonate and saturated brine, dried over magnesium sulfate, filtered and concentrated in vacuum to an orange foam. The foam was dissolved in 175 ml of THF and added to a suspension of approximately 100 g of Raney nickel (Ra-Ni weighed as a slurry in water), which had been washed with water, with 0.5% aqueous acetic acid, again with water and finally with THF. The reaction was stirred at room temperature for 48 hours, then the solution was decanted and the catalyst was washed thoroughly with THF. The combined organic fractions were reduced in volume until a precipitate formed. The title compound (5.15 g, 50%) was isolated as a beige solid, m.p. 233–235° C., by filtration.

Elemental Analysis for: $C_{19}H_{19}NO_6S.0.25$ $H_2O$; Calc'd: C, 57.93; H, 4.99; N, 3.56; Found: C, 57.72; H, 4.96; N, 3.56

EXAMPLE 28

2-[(4-Methyly-benzylamino)-methyl]-6-methyl-2,3,8,9-tetrahydro-7H-1,4-dioxino[2,3-e]indol-8-one (R)-2-(Toluene-4-sulfonyloxymethyl)-6-methyl-2,3,8,9-tetrahydro-7H-1,4-dioxino[2,3-e]indol-8-one (1.20 g, 3.10 mmole) and 4-methylbenzylamine (2.07 g, 17.0 mmole) were combined in 22 ml of dry DMSO and heated to 85° C. for 3.5 hours under a nitrogen atmosphere. After cooling to room temperature, 150 ml of water was added and the mixture was extracted twice with 250 ml portions of 35% ethyl acetate in hexane. The combined organic phases were washed with brine, dried over $MgSO_4$, filtered and concentrated in vacuum to yield 0.38 g of a light yellow solid. The free base of the title compound thus obtained was crystallized from ethanol with the addition of fumaric acid (0.14 g, 1.2 mmole) to give 0.43 g of the (S) enantiomer of the title compound as a yellow solid fumarate, one-quarter ethanolate, m.p. 225–227° C.

Elemental Analysis for: $C_{20}H_{22}N_2O_3.C_4H_4O_4.0.25$ $C_2H_6O$; Calc'd: C, 63.27; H, 5.87; N, 6.08; Found: C, 63.46; H, 5.79; N, 5.97

EXAMPLE 29

2-{[(Thiophene-2-ylmethyl)-amino]-methyl}-6-methyl-2,3,8,9-tetrahydro-7H-1,4-dioxino[2,3-e]indol-8-one (R)-2-(Toluene-4-sulfonyloxymethyl)-6-methyl-2,3,8,9-tetrahydro-7H-1,4-dioxino[2,3-e]indol-8-one (1.00 g, 2.57 mmole) and thiophene-2-methylamine (1.42 g, 12.6 mmole) were combined in 15 ml of dry DMSO and heated to 90° C. for 6 hours under a nitrogen atmosphere. After cooling to room temperature, 250 ml of water was added and a brown solid precipitated This was dissolved in methylene chloride, dried over $MgSO_4$, filtered and concentrated in vacuum to yield an flaky orange solid, which was column chromatographed on silica gel using 1.5% methanol/$CH_2Cl_2$ as eluant. The free base of the title compound (0.27 g) thus obtained was crystallized from isopropanol with the addition of fumaric acid (0.10 g, 0.90 mmole) to give 0.28 g of the (S) enantiomer of the title compound as a light orange solid fumarate, m.p. 211–212° C.

Elemental Analysis for: $C_{17}H_{18}N_2O_3S.C_4H_4O_4$; Calc'd: C, 56.49; H, 4.97; N, 6.27; Found: C, 56.21; H, 4.99; N, 6.14

EXAMPLE 30

6-Methyl-2-{[(naphthalen-1-ylmethyl)-amino]-methyl}-2,3,8,9-7H-tetrahydro-1,4-dioxino[2,3-e]indol-8-one (R)-2-(Toluene-4-sulfonyloxymethyl)-6-methyl-2,3,8,9-tetrahydro-7H-1,4-dioxino[2,3-e]indol-8-one (0.80 g, 2.1 mmole) and 1-naphthalenemethylamine (1.57 g, 10.3 mmole) were combined in 15 ml of dry DMSO and heated to 90° C. for 6 hours under a nitrogen atmosphere. After cooling to room temperature, 250 ml of water was added and the mixture was extracted twice with 250 ml portions of 35% ethyl acetate in hexane. The combined organic phases were washed with brine, dried over $MgSO_4$, filtered and concentrated in vacuum to yield a light orange oil. The oil was column chromatographed on silica gel using 1.5% methanol/ $CH_2Cl_2$ as eluant to yield 0.39 g of the free base of the title compound as a light yellow solid. This was crystallized from isopropanol with the addition of fumaric acid (0.13 g, 1.2 mmole) to give 0.36 g of the (S) enantiomer of the title compound as a light yellow solid fumarate, one-quarter ethanolate, m.p.194–195° C.

Elemental Analysis for: $C_{23}H_{22}N_2O_3 \cdot C_4H_4O_4$; Calc'd: C, 66.11; H, 5.34; N, 5.71; Found: C, 66.03; H, 5.34; N, 5.80

EXAMPLE 31

2-(Benzylamino-methyl)-6-methyl-2,3,8,9-tetrahydro-7H-1,4-dioxino[2,3-e]indol-8-one (R)-2-(Toluene-4-sulfonyloxymethyl)-6-methyl-2,3,8,9-tetrahydro-7H-1,4-dioxino[2,3-e]indol-8-one (1.57 g, 4.04 mmole) and benzylamine (2.18 g, 5.6 mmole) were combined in 10 ml of dry DMSO and heated to 85° C. for 3 hours under a nitrogen atmosphere. After cooling to room temperature, 150 ml of water was added and the mixture was extracted twice with 250 ml portions of 35% ethyl acetate in hexane. The combined organic phases were washed with brine, dried over $MgSO_4$, filtered and concentrated in vacuum to yield an orange oil. Column chromatography on silica gel using 2% methanol/$CH_2Cl_2$ as eluant gave 1.08 g of the free base of the title compound as a light beige solid. This was crystallized from isopropanol with the addition of fumaric acid (0.42 g, 3.7 mmole) to give 0.49 g of the (S) enantiomer of the title compound as a beige solid fumarate, m.p. 219–220° C.

Elemental Analysis for: $C_{19}H_{20}N_2O_3 \cdot C_4H_4O_4$; Calc'd: C, 62.72; H, 5.49; N, 6.36; Found: C, 62.44; H, 5.29; N, 5.57

EXAMPLE 32

2-[(4-Fluoro)-benzylamino-methyl]-6-methyl-2,3,8,9-tetrahydro-7H-1,4-dioxino[2,3-e]indol-8-one (R)-2-(Toluene-4-sulfonyloxymethyl)-6-methyl-2,3,8,9-tetrahydro-7H-1,4-dioxino[2,3-e]indol-8-one (0.28 g, 0.72 mmole) and 4-fluorobenzylamine (0.45 g, 3.6 mmole) were combined in 10 ml of dry DMSO and heated to 90° C. for 4 hours under a nitrogen atmosphere. After cooling to room temperature, 150 ml of water was added and the mixture was extracted twice with 250 ml portions of 35% ethyl acetate in hexane. The combined organic phases were washed with brine, dried over $MgSO_4$, filtered and concentrated in vacuum to yield an orange semisolid. Column chromatography on silica gel using 1% methanol/$CH_2Cl_2$ as eluant gave the free base of the title compound as a brown oil. This was crystallized from isopropanol with the addition of fumaric acid (0.20 g, 1.7 mmole) to give 0.06 g of the (S) enantiomer of the title compound as a beige solid fumarate, m.p. 233–234° C.

Elemental Analysis for: $C_{19}H_{19}FN_2O_3 \cdot C_4H_4O_4$; Calc'd: C, 60.26; H, 5.06; N, 6.11; Found: C, 59.96; H, 4.87; N, 6.14

INTERMEDIATE 12

(R)-2-Toluene-4-sulfonyloxymethyl)-6-fluoro-2,3-dihydrobenzo[1,4]dioxin (S)-(6-flouro-2,3-dihydrobenzo[1,4]dioxin-2-yl)-methanol (17 g, 92 mmole) was dissolved in one liter of pyridine. To this solution was added 38 g (0.20 mole) of p-toluenesulfonyl chloride and the mixture stirred at room temperature under nitrogen for three days. The reaction was cooled in an ice-water bath and to it was added slowly 10 ml of water. The mixture was stirred at room temperature for 2 hours and then the solvent was removed under vacuum and replaced with 800 ml of methylene chloride. This solution was washed twice with 500 ml of 1 N HCl (aq), with saturated aqueous sodium bicarbonate, and with saturated brine and dried over sodium sulfate. Filtration, evaporation in vacuum and column chromatography on silica gel with 50% hexane in dichloromethane as eluent gave 25.1 g (89%) of the title compound as an off-white solid. $^1H$ ($CDCl_3$) doublet, 7.86 δ (2 H); doublet, 7.32 δ (2 H); doublet of doublets, 6.65 δ (1 H); multiplet, 6.58 δ, (2 H); multiplet, 4.34 δ (1 H); multiplet, 4.20 δ (3 H); multiplet, 4.00 δ (1 H); singlet, 2.43 δ (3 H).

INTERMEDIATE 13

(R)-2-Toluene-4-sulfonyloxymethyl)-6-fluoro-7-nitro-2,3-dihydrobenzo[1,4]dioxin (R)-2-Toluene-4-sulfonyloxymethyl)-6-fluoro-2,3-dihydrobenzo[1,4]dioxin (25.1 g, 74 mmole) was dissolved in 250 ml of dichloroethane and cooled to 0° C. in an ice/water bath. To this cooled solution was added dropwise over a 15 minute period a solution of nitric acid (sp. gr. 1.49) in 60 ml of dichloroethane. The mixture was stirred at 0° C. under nitrogen for two hours, after which time the reaction was quenched by the addition of 500 g of ice. The mixture was diluted to 700 ml with methylene chloride and washed with saturated aqueous sodium bicarbonate solution, with water, with saturated brine and dried over sodium sulfate. Filtration and evaporation in vacuum gave 25 g of crude product. This was column chromatographed on silica gel using 1:1 hexane/ethyl acetate as eluant to give 21 g of the title compound as a yellow solid. $^1H$ ($CDCl_3$) doublet, 7.80 δ (2 H); doublet, 7.50 δ (1 H); doublet, 7.38 δ (2 H); doublet, 6.76 δ (1 H); multiplet, 4.40 δ (2 H); multiplet, 4.25 δ (2 H); multiplet, 4.15 δ (1 H); singlet, 2.43 δ (3 H).

INTERMEDIATE 14

(R)-2-Toluene-4-sulfonyloxymethyl)-6-fluoro-7-amino-2,3-dihydrobenzo[1,4]dioxion (R)-2-Toluene-4-sulfonyloxymethyl)-6-fluoro-7-nitro-2,3-dihydrobenzo[1,4]-dioxin (21 g, 55 mmole) was added to a suspension of 2.0 g of 10% palladium on carbon in 250 ml of methanol. To this was added 15 ml of 4 N isopropanolic HCl. The mixture was hydrogenated for 20 hours using a Parr apparatus at 50–60 psi of hydrogen. The mixture was then filtered through celite and the catalyst washed with additional methanol. The filtrate was concentrated in vacuum to give 21.4 g of the title compound as a gray solid hydrochloride. $^1H$ ($DMSO-d_6$) doublet, 7.80 δ (2 H); doublet, 7.47 δ (2 H); doublet, 6.95 δ (1 H); doublet, 6.85 δ (1 H); multiplet, 4.40 δ (1 H); multiplet, 4.25 δ (3 H); multiplet, 4.00 δ (1 H); singlet, 2.40 δ (3 H).

INTERMEDIATE 15

(R)-2-(Toluene-4-sulfonyloxymethyl)-6-fluoro-2,3,8,9-tetrahydro-7H-1,4-dioxino[2,3-e]indol-8-one In a three-neck flask equipped with a dropping funnel, thermometer and a nitrogen inlet was placed 6.15 ml (48.0 mmole) of ethyl methylthioacetate and 65 ml of dry methylene chloride. The solution was cooled to −78° C. by means of a dry ice/isopropanol bath and to it was added dropwise over a 5 minute period a solution of 3.80 g (47.0 mmole) of sulfuryl chloride in 30 ml of methylene chloride. The reaction was maintained at −78° C. for 30 minutes. To the mixture was added dropwise over a one hour period a solution of (R)-2-toluene-4-sulfonyloxymethyl)-6-fluoro-7-amino-2,3-dihydrobenzo[1,4]dioxin (15.7 g, 45.0 mmole) and Proton Sponge (11.7 g, 47.0 mmole) in 150 ml of methylene chloride. The mixture was stirred a −78° C. for two hours, then 9.5 g (54 mmole) of diisopropylethylamine in 20 ml of dichloromethane added dropwise over 10 minutes and stirring continued for an additional hour at −78° C., after which the reaction was allowed to come to room temperature, at which temperature it was stirred for 8 hours under nitrogen. The resulting solution was diluted to 500 ml with methylene chloride and washed with saturated brine, dried over magnesium sulfate, filtered and concentrated in vacuum to a brown oil. This was dissolved in 200 ml of glacial acetic acid and stirred for 10 hours at room temperature under a nitrogen atmosphere. The solvent was then removed in vacuum and replaced with 500 ml of methylene chloride. The mixture was washed with 300 ml portions of saturated aqueous sodium bicarbonate and saturated brine, dried over magnesium sulfate, filtered and concentrated in vacuum to a brown oil, which was column chromatographed on silica gel using 2% methanol in methylene chloride as the eluant. The light brown solid (13.0 g, 66%) thus obtained was dissolved in 200 ml of THF and added to a suspension in 600 ml of THF of approximately 200 g of Raney nickel (Ra-Ni weighed as a slurry in water), which had been washed with water, with 0.5% aqueous acetic acid, again with water and finally with THF. The reaction was stirred at room temperature for 8 hours, then the solution decanted and the catalyst washed thoroughly with THF. The combined organic fractions were concentrated in vacuum and the product column chromatographed on silica gel using methylene chloride as the eluant. The title compound (4.54 g, 40%) was isolated as an off-white solid, m.p. 205–206° C.

Elemental Analysis for: $C_{18}H_{16}FNO_6S.0.25\ H_2O$; Calc'd: C, 54.34; H, 4.18; N, 3.52; Found: C, 54.12; H, 4.24; N, 3.41

EXAMPLE 33

2-(Benzylamino-methyl)-6-fluoro-2,3,8,9-tetrahydro-7H-1,4-dioxino[2,3-e]indol-8-one (R)-2-(Toluene-4-sulfonyloxymethyl)-6-fluoro-2,3,8,9-tetrahydro-7H-1,4-dioxino[2,3-e]indol-8-one (1.0 g, 2.5 mmole) and benzylamine (1.3 g, 12.5 mmole) were combined in 30 ml of dry DMSO and heated at 80–90° C. for 4 hours under an argon atmosphere. After cooling to room temperature, the mixture was diluted with 500 ml of 1:1 ethyl acetate/hexane and washed with 250 ml of saturated aqueous sodium bicarbonate and with two 250 ml portions of water, dried over sodium sulfate, filtered and concentrated in vacuum. The residue was column chromatographed on silica gel using 0.5% methanol/CHCl₃ as eluant to give 0.65 g of the free base of the title compound as a pale yellow oil. This was crystallized from methanol with the addition of one equivalent of fumaric acid to give 0.62 g of the (S) enantiomer of the title compound as a yellow solid fumarate, m.p. 205–207° C.

Elemental Analysis for: $C_{18}H_{17}FN_2O_3.C_4H_4O_4$; Calc'd: C, 59.46; H, 4.76; N, 6.30; Found: C, 59.34; H, 4.81; N, 6.18

EXAMPLE 34

6-Fluoro-2-[(4-fluoro-benzylamino)-methyl]-2,3,8,9-tetrahydro-7H-1,4-dioxino[2,3-e]indol-8-one (R)-2-(Toluene-4-sulfonyloxymethyl)-6-fluoro-2,3,8,9-tetrahydro-7H-1,4-dioxino[2,3-e]indol-8-one (1.0 g, 2.5 mmole) and 4-fluorobenzylamine (1.25 g, 10 mmole) were combined in 30 ml of dry DMSO and heated at 80–90° C. for 4 hours under an argon atmosphere. After cooling to room temperature, the mixture was diluted with 500 ml of 1:1 ethyl acetate/hexane and washed with 250 ml of saturated aqueous sodium bicarbonate and with two 250 ml portions of water, dried over sodium sulfate, filtered and concentrated in vacuum. The residue was column chromatographed on silica gel using 0.5% methanol/CHCl₃ as eluant to give 0.55 g of the free base of the title compound as a pale yellow oil. This was crystallized from ethanol with the addition of one equivalent of fumaric acid to give 0.50 g of the (S) enantiomer of the title compound as a white solid fumarate, m.p. 205–207° C. Elemental Analysis for: $C_{18}H_{16}F_2N_2O_3.C_4H_4O_4$; Calc'd: C, 57.15; H, 4.36; N, 6.06; Found: C, 56.85; H, 4.31; N, 5.92

EXAMPLE 35

6-Fluoro-2-[(4-methyl-benzylamino)-methyl]-9-(4-methyl-benzylidene)-2,3,8,9-tetrahydro-7H-1,4-dioxino[2,3-e]indol-8-one (R)-2-(Toluene-4-sulfonyloxymethyl)-6-fluoro-2,3,8,9-tetrahydro-7H-1,4-dioxino[2,3-e]indol-8-one (1.0 g, 2.5 mmole) and 4-methylbenzylamine (1.2 g, 10 mmole) were combined in 30 ml of dry DMSO and heated at 80° C. for 4 without protection from the atmosphere. After cooling to room temperature, the mixture was concentrated under high vacuum while heating at 100° C. Methylene chloride (300 ml) was added and the solution was washed with 250 ml of saturated aqueous sodium bicarbonate and with saturated brine, dried over sodium sulfate, filtered and concentrated in vacuum. The residue was column chromatographed on silica gel using 0.5% methanol/CHCl₃ as eluant to give 0.51 g of the free base of the title compound as a yellow oil. This was crystallized from ethanol with the addition of one equivalent of fumaric acid to give 049 g of the (S) enantiomer of the title compound as an orange solid fumarate, monohydrate, m.p. 239–241° C.

Elemental Analysis for: $C_{27}H_{25}FN_2O_3.C_4H_4O_4.H_2O$; Calc'd: C, 64.35; H, 5.40; N, 4.84; Found: C, 64.65; H, 5.26; N, 4.60

EXAMPLE 36

6-Fluoro-2-[(4-methyl-benzylamino)-methyl]-2,3,8,9-tetrahydro-7H-1,4-dioxino[2,3-e]indol-8-one (R)-2-(Toluene-4-sulfonyloxymethyl)-6-fluoro-2,3,8,9-tetrahydro-7H-1,4-dioxino[2,3-e]indol-8-one (1.0 g, 2.5 mmole) and 4-methylbenzylamine (1.2 g, 10 mmole) were combined in 30 ml of dry DMSO and heated at 80° C. for 4 hours under an argon atmosphere. After cooling to room temperature, the mixture was diluted with 500 ml of 1:1 ethyl acetate/hexane and washed with 250 ml of saturated aqueous sodium bicarbonate and with two 250 ml portions of water, dried over sodium sulfate, filtered and concentrated in vacuum. The residue was column chromatographed on silica gel using 0.5% methanol/CHCl₃ as eluant and crystallized from ethanol with the addition of fumaric acid to give 0.57 g of the (S) enantiomer of the title compound as an off-white solid fumarate, m.p. 203–204° C.

Elemental Analysis for: $C_{19}H_{19}FN_2O_3.C_4H_4O_4$; Calc'd: C, 60.26; H, 5.06; N, 6.11; Found: C, 60.13; H, 4.90; N, 6.01

EXAMPLE 37

2-{[3-(3-Dimethylamino-phenoxy)-propylamino]-methyl}-6-fluoro-2,3,8,9-tetrahydro-7H-1,4-dioxino[2,3-e]indol-8-one (R)-2-(Toluene-4-sulfonyloxymethyl)-6-fluoro-2,3,8,9-tetrahydro-7H-1,4-dioxino[2,3-e]indol-8-one (1.0 g, 2.5 mmole) and 3-(3-dimethylaminophenoxy)-propylamine (1.92 g, 10 mmole) were combined in 30 ml of dry DMSO and heated at 80–90° C. for 4 hours under an argon atmosphere. After cooling to room temperature, the mixture was diluted with 500 ml of 1:1 ethyl acetate/hexane and washed with 250 ml of saturated aqueous sodium bicarbonate and with two 250 ml portions of water, dried over sodium sulfate, filtered and concentrated in vacuum. The residue was column chromatographed on silica gel using 1% methanol/CHCl$_3$ as eluant to give 0.25 g of the free base of the title compound as a yellow oil. This was crystallized from ethanol with the addition of one equivalent of fumaric acid to give 0.19 g of the (S) enantiomer of the title compound as a tan solid fumarate, m.p. 121–123° C.

Elemental Analysis for: $C_{22}H_{26}FN_3O_4 \cdot C_4H_4O_4$; Calc'd: C, 58.75; H, 5.69; N, 7.91; Found: C, 58.95; H, 5.73; N, 8.09

EXAMPLE 38

2-{[(Adamantan-1-ylmethyl)-amino]-methyl}-6-fluoro-2,3,8,9-tetrahydro-7H-1,4-dioxino[2,3-e]indol-8-one (R)-2-(Toluene-4-sulfonyloxymethyl)-6-fluoro-2,3,8,9-tetrahydro-7H-1,4-dioxino[2,3-e]indol-8-one (1.0 g, 2.5 mmole) and 1-adamantylmethylamine (1.6 g, 10 mmole) were combined in 30 ml of dry DMSO and heated at 80–90° C. for 4 hours under an argon atmosphere. After cooling to room temperature, the mixture was diluted with 500 ml of 1:1 ethyl acetate/hexane and washed with 250 ml of saturated aqueous sodium bicarbonate and with two 250 ml portions of water, dried over sodium sulfate, filtered and concentrated in vacuum. The residue was column chromatographed on silica gel using 0.5% methanol/CHCl$_3$ as eluant to give 0.70 g of the free base of the title compound as a colorless oil. This was crystallized from ethanol with the addition 4 N isopropanolic HCl to give 0.54 g of the (S) enantiomer of the title compound as a fluffy white solid hydrochloride, m.p.>260° C.

Elemental Analysis for: $C_{22}H_{27}FN_2O_3 \cdot HCl$; Calc'd: C, 62.48; H, 6.67; N, 6.62; Found: C, 62.13; H, 6.82; N, 6.56

EXAMPLE 39

6-Fluoro-2-{[3-(1H-indol-3-yl)-propylamino]-methyl}-2,3,8,9-tetrahydro-7H-1,4-dioxino[2,3-e]indol-8-one (R)-2-(Toluene-4-sulfonyloxymethyl)-6-fluoro-2,3,8,9-tetrahydro-7H-1,4-dioxino[2,3-e]indol-8-one (1.0 g, 2.5 mmole) and 3-(3-aminopropyl)indole (1.74 g, 10 mmole) were combined in 30 ml of dry DMSO and heated at 80–90° C. for 4 hours under an argon atmosphere. After cooling to room temperature, the mixture was diluted with 500 ml of 1:1 ethyl acetate/hexane and washed with 250 ml of saturated aqueous sodium bicarbonate and with two 250 ml portions of water, dried over sodium sulfate, filtered and concentrated in vacuum. The residue was column chromatographed on silica gel using 0.5% methanol/CHCl$_3$ as eluant to give 0.33 g of the free base of the title compound as a pale yellow oil. This was crystallized from ethanol with the addition of one equivalent of fumaric acid to give 0.29 g of the (S) enantiomer of the title compound as a yellow solid fumarate, m.p. 133° C.

Elemental Analysis for: $C_{22}H_{22}FN_3O_3 \cdot C_4H_4O_4$; Calc'd: C, 61.05; H, 5.12; N, 8.21; Found: C, 61.39; H, 5.40; N, 8.24

EXAMPLE 40

2-[(4-Chloro-benzylamino)-methyl]-6-fluoro-2,3,8,9-tetrahydro-7H-1,4-dioxino[2,3-e]indol-8-one (R)-2-(Toluene-4-sulfonyloxymethyl)-6-fluoro-2,3,8,9-tetrahydro-7H-1,4-dioxino[2,3-e]indol-8-one (0.55 g, 1.4 mmole) and 4-chlorobenzylamine (1.4 g, 10 mmole) were combined in 40 ml of dry DMSO and heated at 100° C. for 6 hours under an argon atmosphere. After cooling to room temperature, the mixture was diluted with 500 ml of 1:1 ethyl acetate/hexane and washed with 250 ml of saturated aqueous sodium bicarbonate and with two 250 ml portions of water, dried over sodium sulfate, filtered and concentrated in vacuum. The residue was column chromatographed on silica gel using 0.5% methanol/CHCl$_3$ as eluant to give 0.13 g of the free base of the title compound as a pale yellow oil. This was crystallized from ethanol with the addition of one equivalent of (R)-mandelic acid to give 0.06 g of the (S) enantiomer of the title compound as a peach solid (R)-mandelate, m.p. 187–188° C.

Elemental Analysis for: $C_{18}H_{16}ClFN_2O_3 \cdot C_8H_8O_3$; Calc'd: C, 60.65; H, 4.70; N, 5.44; Found: C, 60.48; H, 4.49; N, 5.37

EXAMPLE 41

6-Fluoro-2-[(4-trifluoromethyl-benzylamino)-methyl]-2,3,8,9-tetrahydro-7H-1,4-dioxino[2,3-e]indol-8-one (R)-2-(Toluene-4-sulfonyloxymethyl)-6-fluoro-2,3,8,9-tetrahydro-7H-1,4-dioxino[2,3-e]indol-8-one (0.93 g, 2.37 mmole) and 4-trifluoromethylbenzylamine (1.65 ml, 11.6 mmole) were combined in 13 ml of dry DMSO and heated at 85° C. for 3.5 hours under nitrogen. After cooling to room temperature, 200 ml of water was added and the mixture was extracted with two 250 ml portions of 1:1 ethyl acetate/hexane and the combined extracts washed with brine, dried over magnesium sulfate, filtered and concentrated in vacuum. The residue was column chromatographed on silica gel using 2% methanol/CH$_2$Cl$_2$ as eluant to give 0.70 g of the free base of the title compound as a yellow oil. This was crystallized from ethanol with the addition of one equivalent of fumaric acid to give 0.32 g of the (S) enantiomer of the title compound as a white solid fumarate, three-quarter hydrate, m.p. 192° C.

Elemental Analysis for: $C_{19}H_{16}F_4N_2O_3 \cdot C_4H_4O_4 \cdot 0.75 H_2O$; Calc'd: C, 52.53; H, 4.12; N, 5.33; Found: C, 52.27; H, 3.85; N, 5.28

EXAMPLE 42

6-Fluoro-2-[(4-phenyl-butylamino)-methyl]-2,3,8,9-tetrahydro-7H-1,4-dioxino[2,3-e]indol-8-one (R)-2-(Toluene-4-sulfonyloxymethyl)-6-fluoro-2,3,8,9-tetrahydro-7H-1,4-dioxino[2,3-e]indol-8-one (0.85 g, 2.16 mmole) and 4-phenylbutylamine (1.55 ml, 9.8 mmole) were combined in 20 ml of dry DMSO and heated at 85° C. for 3.5 hours under nitrogen. After cooling to room temperature, 200 ml of water was added and the mixture was extracted with two 250 ml portions of 1:1 ethyl acetate/hexane and the combined extracts washed with brine, dried over magnesium sulfate, filtered and concentrated in vacuum. The residue was column chromatographed on silica gel using 0.5% methanol/CH$_2$Cl$_2$ as eluant to give 0.40 g of the free base of the title compound as a yellow oil. This was crystallized from ethanol with the addition of one equivalent of fumaric acid to give 0.33 g of the (S) enantiomer of the title compound as a light yellow solid hemifumarate, one-quarter hydrate, m.p. 164° C.

Elemental Analysis for: $C_{21}H_{23}FN_2O_3 \cdot 0.5 C_4H_4O_4 \cdot 0.25 H_2O$; Calc'd: C, 63.80; H, 5.94; N, 6.47; Found: C, 63.81; H, 5.75; N, 6.33

INTERMEDIATE 16

2-Allyloxy-5-chlorophenol

To 14 g (0.35 mole) of 60% sodium hydride/mineral oil dispersion in a two liter flask was added 500 ml of hexane. The mixture was swirled briefly, the solid allowed to settle and the supernatant liquid decanted. DMF (800 ml) was added, followed by a solution of 47 g (0.30 mole) of 5-chlorosalicylaldehyde in 50 ml of DMF. The mixture was stirred at room temperature under nitrogen for 30 minutes, then 54.5 g (0.45 mole) of allyl bromide was added. The mixture was heated at 65° C. under nitrogen for 18 hours. The solvent was then removed in vacuum and replaced with one liter of methylene chloride. This solution was washed with water and with saturated brine and dried over sodium sulfate. It was then filtered and 150 g (0.50–0.75 mole) of 57–86% m-chloroperoxybenzoic acid added and the mixture stirred at room temperature overnight. The reaction was filtered and the filtrate washed with three 400 ml portions of saturated aqueous sodium bicarbonate and with saturated brine, dried over sodium sulfate, filtered and concentrated in vacuum. The residue was dissolved in 750 ml of methanol and stirred with 150 g of basic alumina for 15 hr. The mixture was then filtered and evaporated in vacuum and the crude product partitioned between 500 ml each of 1 N NaOH (aq) and methylene chloride. The organic phase was extracted with an additional 500 ml of base, and the combined basic extracts back-washed with 500 ml of methylene chloride. Finally, the basic extracts were carefully acidified with concentrated HCl and extracted with two 400 ml portions of methylene chloride. The combined organic extracts were washed with saturated brine, dried over sodium sulfate, filtered and concentrated in vacuum to give 37.3 g of the title compound as a yellow oil. $^1$H (CDCl$_3$) singlet, 6.90 δ (1 H); quartet, 6.70 δ (2 H); singlet, 6.20 δ (1 H, OH);.multiplet, 5.97 δ (1 H); quartet, 5.25 δ (2 H); doublet, 4.50 δ (2 H).

INTERMEDIATE 17

(R)-2-(2-Allyloxy-5-chlorophenoxymethyl)-oxirane

To 4.0 g (79 mmole) of 60% sodium hydride/mineral oil dispersion in a one liter flask was added 300 ml of hexane. The mixture was swirled briefly, the solid allowed to settle and the supernatant liquid decanted. DMF (500 ml) was added, followed by a solution of 14.6 g (79 mmole) of 2-allyloxy-5-chlorophenol in 100 ml of DMF. The mixture was stirred at room temperature under nitrogen for 30 minutes, then 18.0 g (79 mmole) of (R)-glycidyl tosylate added. The mixture was heated under a nitrogen atmosphere at 80° C. for 24 hours. The solvent was evaporated in vacuum and replaced with 750 ml of methylene chloride. The solution was washed with 500 ml portions of 2 N HCl (aq), saturated aqueous sodium bicarbonate, saturated brine, dried over sodium sulfate, filtered and evaporated in vacuum to give 20 g of a crude gum. This was column chromatographed on silica gel using methylene chloride as eluant to give 9.2 g of the title compound as a colorless oil. $^1$H (CDCl$_3$) singlet, 6.93 δ (1 H); doublet, 6.90 δ (1 H); doublet, 6.80 δ (1 H);.multiplet, 6.05 δ (1 H); doublet, 5.40 δ (1 H); doublet, 5.25 δ (1 H); doublet, 4.55 δ (2 H); doublet of doublets, 4.25 δ (1 H); doublet of doublets, 3.97 δ (1 H); multiplet, 3.35 δ (1 H); triplet, 2.95 δ (2H); triplet, 2.75 δ (1 H).

INTERMEDIATE 18

(S)-(8-Allyl-6-chloro-2,3-dihydro-benzo(1,4)dioxin-2-yl)-methanol (R)-2-(2-Allyloxy-5-chlorophenoxymethyl)-oxirane (9.2 g, 38 mmole) was dissolved in 500 ml of mesitylene and refluxed under nitrogen for 48 hours. The solvent was then removed in vacuum and replaced with 500 ml of ethanol. Sodium bicarbonate (50 g, 0.60 mole) was added and the mixture stirred at room temperature under nitrogen for 24 hours. The mixture was then filtered and concentrated in vacuum. The solvent was replaced with 500 ml of methylene chloride and the solution was washed with water and with saturated brine, dried over sodium sulfate, filtered and evaporated in vacuum. The residue was column chromatographed on silica gel using chloroform as eluant to give 8.9 g of the title compound as a colorless oil. $^1$H (CDCl$_3$) singlet, 6.80 δ (1 H); singlet, 6.73 δ (1 H); multiplet, 5.95 δ (1 H); doublet, 5.10 δ (1 H); doublet, 5.05 δ (1 H); multiplet, 4.25 δ (2 H); multiplet, 4.10 δ (1 H); multiplet, 3.85 δ (2 H); multiplet, 3.30 δ (2 H); broad singlet, 2.00 δ (1 H).

INTERMEDIATE 19

Toluene-4-sulfonic acid (R)-8-allyl-6-chloro-2,3-dihydro-benzo(1,4)dioxin-2-ylmethyl ester 8.9 g (37 mmole) of (S)-(8-allyl-6-chloro-2,3-dihydro-benzo(1,4)dioxin-2-yl)-methanol was dissolved in 500 ml of pyridine, 14.3 g (75 mmole) of p-toluenesulfonyl chloride was added and the mixture stirred at room temperature under nitrogen for 3 days. Water was then added to quench the excess tosyl chloride and the solvent was removed in vacuum and replaced with 500 ml of methylene chloride. This solution was washed twice with 300 ml of 2N HCl (aq), with saturated sodium bicarbonate, and with saturated brine, and dried over sodium sulfate. Filtration, evaporation in vacuum and column chromatography on silica gel with 1:1 hexane/methylene chloride as eluant gave 10.9 g of the desired tosylate as a colorless oil. $^1$H (CDCl$_3$) doublet, 7.80 δ (2 H); doublet, 7.30 δ (2 H); singlet, 6.75 δ (1 H);.singlet, 6.70 δ (1H); multiplet, 5.85 δ (1 H); singlet, 5.08 δ (1 H); doublet, 5.03 δ (1 H); multiplet, 4.40 δ (1 H); multiplet, 4.20 δ (2 H); doublet of doublets, 4.05 δ (1 H); multiplet, 3.20 δ (2H); singlet, 2.45 δ (3 H).

INTERMEDIATE 20

(R)-(7-Chloro-3-(toluene-4-sulfonyloxymethyl)-2,3-dihydro-benzo(1,4)dioxin-5-yl)-acetic acid Potassium permanganate (14 g, 87 mmole) was dissolved in 140 ml of water and placed in a water bath. To this was added 1.4 g (4.9 mmole) of tetra-n-butylammonium chloride and then a solution of 10.9 g of toluene-4-sulfonic acid (R)-8-allyl-6-chloro-2,3-dihydro-benzo(1,4)dioxin-2-ylmethyl ester (28 mmole) in 100 ml of benzene was added dropwise over a 30 minute period. The mixture was stirred at room temperature overnight. Sodium bisulfite (17 g, 0.12 mole) was then added and the mixture acidified with concentrated HCl and extracted with two 300 ml portions of ethyl acetate. The combined extracts were washed with water and with saturated brine and dried over sodium sulfate. Filtration, concentration in vacuum and column chromatography with silica gel using 3% methanol in methylene chloride gave 5.9 g of the title compound as a viscous yellow oil. $^1$H (CDCl$_3$) doublet, 7.75 δ (2 H); doublet, 7.35 δ (2 H); singlet, 6.78 δ (1 H);.singlet, 6.75 δ (1 H); multiplet, 4.40 δ (1 H); multiplet, 4.20 δ (3 H); doublet of doublets, 4.05 δ (1 H); collapsed AB quartet, 3.50 δ (2H); singlet, 2.45 δ (3 H).

INTERMEDIATE 21

(R)-(7-Chloro-6-nitro-3-(toluene-4-sulfonyloxymethyl)-2,3-dihydro-benzo(1,4)dioxin-5-yl)-acetic acid To 3.0 g (7.3 mmole) of (R)-(7-chloro-3-(toluene-4-sulfonyloxymethyl)-2,3-dihydro-benzo(1,4)dioxin-5-yl)- acetic acid in 50 of dichloroethane in an ice/water bath was added a solution of 3.6 ml (85 mmole) of nitric acid (sp. gr. 1.49) in 50 ml of dichloroethane. The mixture was allowed to come to room temperature and stir overnight. Ice was added to quench the reaction and the mixture was diluted to 300 ml with methylene chloride, washed with water and with saturated brine and dried over sodium sulfate. Concentration in vacuum gave 2.8 g of the title compound as an off-white solid. $^1$H (DMSO-d$_6$) broad singlet, 12.75 δ (1 H); doublet, 7.80 δ (2 H); doublet, 7.45 δ (2 H);.singlet, 7.15 δ (1 H); multiplet, 4.60 δ (1 H); multiplet, 4.37 δ (2 H); multiplet, 4.15 δ (2 H); singlet, 3.45 δ (2H); singlet, 2.40 δ (3 H).

INTERMEDIATE 22

(R)-2-(Toluene-4-sulfonyloxymethyl)-6-chloro-2,3, 8,9-tetrahydro-7H-1,4-dioxino[2,3-e]indol-8-one To a solution of 2.8 g (6.1 mmole) of (R)-(7-chloro-6-nitro-3-(toluene-4-sulfonyloxymethyl)-2,3-dihydro-benzo (1,4)dioxin-5-yl)-acetic acid in 200 ml of methanol was added 100 mg of platinum oxide. The mixture was hydrogenated on a Parr apparatus at 50 psi for 4 hours. The mixture was filtered through celite and concentrated in vacuum to give 2.8 g of crude amino acid. This was redissolved in 250 ml of methanol and 50 ml of 4 N isopropanolic HCl added. The mixture was heated at 50° C. for 24 hours. The solvent was removed in vacuum and 400 ml of ethyl acetate added. This solution was washed with 200 ml of water, 200 ml of saturated aqueous sodium bicarbonate and saturated brine, dried over sodium sulfate, filtered and concentrated in vacuum. The residue was column chromatographed on silica gel using 1% methanol in methylene chloride as eluant to give 1.4 g of the title compound as an off-white solid. $^1$H (DMSO-d$_6$) singlet, 10.63 δ (1 H); doublet, 7.80 δ (2 H); doublet, 7.45 δ (2 H);.singlet, 6.75 δ (1 H); multiplet, 4.55 δ (1 H); multiplet, 4.35 δ (1 H); multiplet, 4.20 δ (2 H); doublet of doublets, 4.03 δ (2H); ABquartet, 3.25 δ (2 H); singlet, 2.40 δ (3 H).

EXAMPLE 43

6-Chloro-2-[(4-chloro-benzylaminno)-methyl]-2,3,8, 9-tetrahydro-7H-1,4-dioxino[2,3-e]indol-8-one (R)-2-(Toluene-4-sulfonyloxymethyl)-6-chloro-2,3,8,9-tetrahydro-7H-1,4-dioxino[2,3-e]indol-8-one (0.80 g, 2.0 mmole) and 4-chlorobenzylamine (1.1 g, 8.0 mmole) were combined in 25 ml of dry DMSO and heated at 80–90° C. for 4 hours under an argon atmosphere. After cooling to room temperature, the mixture was diluted with 500 ml of 1:1 ethyl acetate/hexane and washed with 250 ml of saturated aqueous sodium bicarbonate and with two 250 ml portions of water, dried over sodium sulfate, filtered and concentrated in vacuum. The residue was column chromatographed on silica gel using 0.5% methanol/CHCl$_3$ as eluant to give 0.36 g of the free base of the title compound as a pale yellow oil. This was crystallized from ethanol with the addition of one equivalent of fumaric acid to give 0.28 g of the (S) enantiomer of the title compound as a tan solid fumarate, hemihydrate, m.p. 207–209° C.

Elemental Analysis for: $C_{18}H_{16}ClN_2O_3 \cdot C_4H_4O_4 \cdot 0.5\ H_2O$; Calc'd: C, 52.39; H, 4.20; N, 5.55; Found: C, 52.37; H, 4.01; N, 5.61

EXAMPLE 44

6-Chloro-2-[(4-methyl-benzylamino)-methyl]-2,3,8, 9-tetrahydro-7H-1,4-dioxino[2,3-e]indol-8-one (R)-2-(Toluene-4-sulfonyloxymethyl)-6-chloro-2,3,8,9-tetrahydro-7H-1,4-dioxino[2,3-e]indol-8-one (0.80 g, 2.0 mmole) and 4-methylbenzylamine (1.0 g, 8.0 mmole) were combined in 25 ml of dry DMSO and heated at 80–90° C. for 4 hours under an argon atmosphere. After cooling to room temperature, the mixture was diluted with 500 ml of 1:1 ethyl acetate/hexane and washed with 250 ml of saturated aqueous sodium bicarbonate and with two 250 ml portions of water, dried over sodium sulfate, filtered and concentrated in vacuum. The residue was column chromatographed on silica gel using 0.5% methanol/CHCl$_3$ as eluant to give 0.43 g of the free base of the title compound as a pale yellow oil. This was crystallized from ethanol with the addition of one equivalent of fumaric acid to give 0.32 g of the (S) enantiomer of the title compound as a white solid fumarate, m.p. 218–219° C.

Elemental Analysis for: $C_{19}H_{19}ClN_2O_3 \cdot C_4H_4O_4$; Calc'd: C, 58.17; H, 4.88; N, 5.90; Found: C, 57.84; H, 4.53; N, 5.97

EXAMPLE 45

2-(Benzylamino)-methyl-6-chloro-2,3,8,9-tetrahydro-7H-1,4-dioxino[2,3-e]indol-8-one (R)-2-(Toluene-4-sulfonyloxymethyl)-6-chloro-2,3,8,9-tetrahydro-7H-1,4-dioxino[2,3-e]indol-8-one (0.80 g, 2.0 mmole) and benzylamine (0.86 g, 8.0 mmole) were combined in 25 ml of dry DMSO and heated at 80–90° C. for 4 hours under an argon atmosphere. After cooling to room temperature, the mixture was diluted with 500 ml of 1:1 ethyl acetate/hexane and washed with 250 ml of saturated aqueous sodium bicarbonate and with two 250 ml portions of water, dried over sodium sulfate, filtered and concentrated in vacuum. The residue was column chromatographed on silica gel using 0.5% methanol/CHCl$_3$ as eluant to give 0.33 g of the free base of the title compound as a pale yellow oil. This was crystallized from ethanol with the addition of one equivalent of fumaric acid to give 0.28 g of the (S) enantiomer of the title compound as a white solid fumarate, m.p. 192–193° C.

Elemental Analysis for: $C_{18}H_{17}ClN_2O_3 \cdot C_4H_4O_4$; Calc'd: C, 57.34; H, 4.59; N, 6.08; Found: C, 57.45; H, 4.48; N, 6.26

EXAMPLE 46

6-Chloro-2-[(4-fluoro-benzylamino)-methyl]-2,3,8, 9-tetrahydro-7H-1,4-dioxino[2,3-e]indol-8-one (R)-2-(Toluene-4-sulfonyloxymethyl)-6-chloro-2,3,8,9-tetrahydro-7H-1,4-dioxino[2,3-e]indol-8-one (0.80 g, 2.0 mmole) and 4-fluorobenzylamine (1.0 g, 0.80 mmole) were combined in 25 ml of dry DMSO and heated at 80–90° C. for 4 hours under an argon atmosphere. After cooling to room temperature, the mixture was diluted with 500 ml of 1:1 ethyl acetate/hexane and washed with 250 ml of saturated aqueous sodium bicarbonate and with two 250 ml portions of water, dried over sodium sulfate, filtered and concentrated in vacuum. The residue was column chromatographed on silica gel using 0.5% methanol/CHCl$_3$ as eluant to give 0.41 g of the free base of the title compound as a pale yellow oil. This was crystallized from ethanol with the addition of one equivalent of fumaric acid to give 0.29 g of the (S) enantiomer of the title compound as a yellow solid fumarate, one-quarter hydrate, m.p. 213–214° C.

Elemental Analysis for: $C_{18}H_{16}ClFN_2O_3 \cdot C_4H_4O_4 \cdot 0.25\ H_2O$; Calc'd: C, 54.67; H, 4.27; N, 5.79; Found: C, 54.54; H, 4.08; N, 5.60

What is claimed is:

1. A compound of formula I

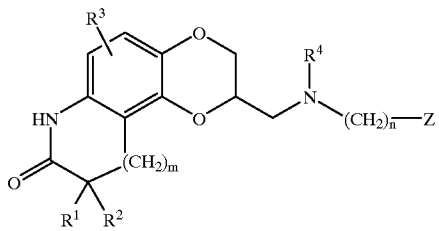

wherein
- $R^1$ and $R^2$ are, independently, hydrogen, alkyl of 1 to 6 carbon atoms, phenyl or benzyl; or $R^1$ and $R^2$, taken together, are benzylidene optionally substituted with $R^3$ as defined below or alkylidene of up to 6 carbon atoms, or $R^1$ and $R^2$, taken together with the carbon to which they are attached, form a carbonyl moiety or a cycloalkyl group having three to 6 carbon atoms;
- $R^3$ is hydrogen, hydroxy, halo, trifluoromethyl, trifluoromethoxy, alkyl of 1 to 6 carbon atoms, alkoxy of 1 to 6 carbon atoms, arylalkoxy of 7 to 12 carbon atoms, alkanoyloxy of 2 to 6 carbon atoms, amino, mono- or di-alkylamino in which each alkyl group has 1 to 6 carbon atoms, alkanamido of 2 to 6 carbon atoms or alkanesulfonamido of 1 to 6 carbon atoms;
- $R^4$ is hydrogen or alkyl of 1 to 6 carbon atoms;
- m is 1;
- n is one of the integers 0, 1, 2, 3, 4, 5, or 6;
- Z is hydrogen, hydroxy, alkyl of 1 to 6 carbon atoms, alkenyl of 2 to 6 carbon atoms, alkynyl of 2 to 6 carbon atoms, alkoxy of 1 to 6 carbon atoms, cycloalkyl of 3 to 8 carbon atoms, polycyclic alkyl of 7 to 15 carbon atoms, phenyl optionally substituted with $R^3$ as defined above, phenoxy optionally substituted with $R^3$ as defined above, naphthyl optionally substituted with $R^3$ as defined above or naphthyloxy optionally substituted with $R^3$ as defined above, heteroaryl or heteroaryloxy, in which the heterocyclic ring of the heteroaryl or heteroaryloxy group is selected from thiophene, furan, pyridine, pyrazine, pyrimidine, indole, indazole, imidazole, chroman, coumarin, carbostyril, quinoline, benzisoxazole, benzoxazole, pyrazole, pyrrole, thiazole, oxazole, or isoxazole and the heterocyclic ring is optionally substituted by $R^3$ as defined above;

or a pharmaceutically acceptable salt thereof.

2. A compound of claim 1 in which $R^1$ and $R^2$ are hydrogen or together form benzylidene optionally substituted with $R^3$ as defined in claim 1 or, taken together with the carbon to which they are attached, form a carbonyl moiety; $R^4$ is hydrogen; m is 1; and Z is hydrogen, hydroxy, alkyl of 1 to 6 carbon atoms, cycloalkyl of 3 to 8 carbon atoms, polycyclic alkyl of 7 to 15 carbon atoms, phenyl optionally substituted with $R^3$ as defined in claim 1, phenoxy optionally substituted with $R^3$ as defined in claim 1, naphthyl optionally substituted with $R^3$ as defined in claim 1 or naphthyloxy optionally substituted with $R^3$ as defined in claim 1, heteroaryl or heteroaryloxy, in which the heterocyclic ring of the heteroaryl or heteroaryloxy group is selected from thiophene, furan, pyridine, pyrazine, pyrimidine, indole, indazole, imidazole, chroman, coumarin, carbostyril, quinoline, benzisoxazole, benzoxazole, pyrazole, pyrrole, thiazole, oxazole, or isoxazole and the heterocyclic ring is optionally substituted by $R^3$ as defined in claim 1; or a pharmaceutically acceptable salt thereof.

3. The compound of claim 1 which is 2-(benzylaminomethyl)-2,3,9,10-tetrahydro-7H-1,4-dioxino[2,3-f]quinolin-8-one or a pharmaceutically acceptable salt thereof.

4. A method for treatment of diseases of brain dopamine dysregulation, which comprises administering, orally or parenterally, to a subject suffering from such a disorder of the dopaminergic system, an amount of a compound of formula I

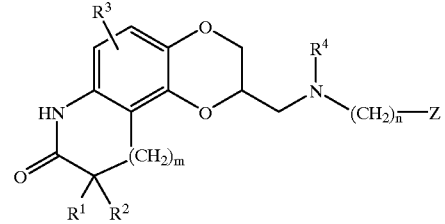

wherein
- $R^1$ and $R^2$ are, independently, hydrogen, alkyl of 1 to 6 carbon atoms, phenyl or benzyl; or $R^1$ and $R^2$, taken together, are benzylidene optionally substituted with $R^3$ as defined below or alkylidene of one to 6 carbon atoms, or $R^1$ and $R^2$, taken together with the carbon to which they are attached, form a carbonyl moiety or a cycloalkyl group having up to 6 carbon atoms;
- $R^3$ is hydrogen, hydroxy, halo, trifluoromethyl, trifluoromethoxy, alkyl of 1 to 6 carbon atoms, alkoxy of 1 to 6 carbon atoms, aralkoxy of 7 to 12 carbon atoms, alkanoyloxy of 2 to 6 carbon atoms, amino, mono- or di-alkylamino in which each alkyl group has 1 to 6 carbon atoms, alkanamido of 2 to 6 carbon atoms or alkanesulfonamido of 1 to 6 carbon atoms;
- $R^4$ is hydrogen or alkyl of 1 to 6 carbon atoms;
- m is one 1,
- n is one of the integers 0, 1, 2, 3, 4, 5 or 6;
- Z is hydrogen, hydroxy, alkyl of 1 to 6 carbon atoms, alkenyl of 2 to 6 carbon atoms, alkynyl of 2 to 6 carbon atoms, alkoxy of 1 to 6 carbon atoms, cycloalkyl of 3 to 8 carbon atoms, polycyclic alkyl of 7 to 15 carbon atoms, phenyl optionally substituted with $R^3$ as defined above, phenoxy optionally substituted with $R^3$ as defined above, naphthyl optionally substituted with $R^3$ as defined above or naphthyloxy optionally substituted with $R^3$ as defined above, heteroaryl or heteroaryloxy, in which the heterocyclic ring of the heteroaryl or heteroaryloxy group is selected from thiophene, furan, pyridine, pyrazine, pyrimidine, indole, indazole, imidazole, chroman, coumarin, carbostyril, quinoline, benzisoxazole, benzoxazole, pyrazole, pyrrole, thiazole, oxazole, or isoxazole and the heterocyclic ring is optionally substituted by $R^3$ as defined above;

or a pharmaceutically acceptable salt thereof;

sufficient to alleviate the symptoms of brain dopamine dysregulation.

* * * * *